United States Patent [19]
Hansen et al.

[11] Patent Number: 6,063,915
[45] Date of Patent: May 16, 2000

[54] CARRAGEENAN COMPOSITIONS AND METHODS FOR THEIR PRODUCTION

[75] Inventors: Jack Harbo Hansen, Taastrup; Jan Groendal, Jyllinge; Henrik Larsen, Vanloese, all of Denmark

[73] Assignee: Hercules Incorporated, Wilmington, Del.

[21] Appl. No.: 09/124,970

[22] Filed: Jul. 30, 1998

[51] Int. Cl.$^7$ .................................................. C07G 17/00
[52] U.S. Cl. .......................... 536/114; 536/123; 536/128; 536/122; 435/240.45; 426/575; 426/584
[58] Field of Search .................................. 536/114, 123, 536/128, 122; 435/240.45; 426/575, 584

[56] References Cited

U.S. PATENT DOCUMENTS

| | | |
|---|---|---|
| 2,620,335 | 12/1952 | Nielson . |
| 2,624,727 | 1/1953 | Legloahec . |
| 3,094,517 | 6/1963 | Stanley . |
| 3,176,003 | 3/1965 | Stancioff . |
| 3,342,612 | 9/1967 | Foster et al. . |
| 3,556,810 | 1/1971 | Moirano . |
| 3,907,770 | 9/1975 | Strong . |
| 4,276,320 | 6/1981 | Moirano . |
| 5,502,179 | 3/1996 | Larsen . |

FOREIGN PATENT DOCUMENTS

| | | |
|---|---|---|
| 0271131 | 1/1993 | European Pat. Off. . |
| 82131202 | 8/1982 | Japan . |
| 84113002 | 6/1984 | Japan . |
| 64-7081 | 2/1989 | Japan . |
| 89007602 | 2/1989 | Japan . |
| 1-59282 | 12/1989 | Japan . |

OTHER PUBLICATIONS

Copy of English Language Abstract of JP No. 89007602.

Ciancia, M. et al., *Carbohydrate Polymers*, 32 (1997), pp. 293–295.

Chapter 7 of *Industrial Gums: Polysaccharides and Their Derivatives, Third Ed.,* (Whistler and BeMiller, eds., Academic Press, San Diego 1993).

Chapter 3 of *Thickening and Gelling Agents for Food, Second Edition,* (Imeson, ed. Chapman & Hall, NY 1997).

Nijenhuis, K., in *Advances in Polymer Science,* 130 (1997), pp. 203–218.

Stortz, C.A., and Cerezo, A.S., *Carbohydrate Research* 145 (1986), pp. 219–235.

Copenhagen Pectin "Carrageenan: General Description".

Smith et al., *Canadian Journal of Chemistry*, vol. 33, pp. 1352–1360, 1955.

Chemical Abstracts, vool. 101, No. 16, Oct. 15, 1984, abstract No. 132893, XP00298545.

Ciancia et al., "Alkaline Modification of Carrageenans, Part III. Use of Mld Alkaline Media andd High Ionic Strengths," *Carbohydrate Polymers,* vol. 32, No. 3–4, Mar. 1997, pp. 293–295.

Patent Abstracts of Japan, vol. 006, No. 227 (C–134), Nov. 12, 1982.

*Primary Examiner*—Keith D. MacMillan
*Assistant Examiner*—Vickie Kim
*Attorney, Agent, or Firm*—Greenblum & Bernstein P.L.C.

[57] ABSTRACT

Carrageenan compostions comprising from about from about 79 mol % to about 95 mol % iota carrageenan and from about 0.1 mol % to about 10 mol % nu carrageenan, and carrageenan and compositions which exhibit elastic modulus, G'—1 Hz at 5° C., of greater than about 200 Pa, elastic modulus, G'—1 Hz at 25° C., of less than about 200 Pa, viscous modulus, G"—0.2 Hz at 5° C., of from about 5 Pa to about 25 Pa, and melting point of less than 60° C., in a 1.2 wt % aqueous gel, and methods of producing the same.

56 Claims, 3 Drawing Sheets

Water Jellies
Sensory Profile

CARRAGEENAN COMPOSITIONS AND METHODS FOR THEIR PRODUCTION

BACKGROUND OF THE INVENTION

1. Field of the Invention

The present invention relates to carrageenan compositions, and to methods for producing carrageenan compositions. The present invention further relates to products containing carrageenan compositions.

2. Background of the Invention and Related Information

For a variety of applications there is a need for aqueous gels that have a high degree of temperature sensitivity. For example, in food products there is often a need for a gel which has a gummy texture, a high degree of cohesiveness and displays bounciness at low temperatures of about 5 to 15° C., yet readily melts in the mouth of the consumer at temperatures of about 25 to 37° C. Similarly for applications such as aqueous gel cosmetics and pharmaceutical products for topical application to the skin, it is also desirable to have a gel component that is firm at lower temperatures yet softens at or near human body temperature.

The most popular of these gelling agents is gelatin, a heterogeneous mixture of water-soluble proteins of high average molecular weight. Gelatin does not occur naturally, but is derived from collagen using a hydrolytic process. Gelatin is usually obtained by boiling bovine or swine skin, tendons, ligaments, bones, etc., but may also be obtained from fish skin.

In its gelling qualities, gelatin is unsurpassed. It is superlative in its gel strength, gel strength loss, lack of gumminess, and "ring." However, because it is necessarily derived from animals, it suffers its own unique drawbacks. For example, gelatin is unacceptable to those of Jewish and Muslim faith, as it is usually prepared from swine skin. Additionally, the safety of the use of gelatin in foods has recently been questioned because of the possible link between consumption of foods prepared from bovine renderings and the occurrence of the fatal Creutzfeldt-Jakob disease. Finally, there are those who are ethically opposed to the consumption of animals or animal-derived products.

For the foregoing reasons, there is a desire, and a need, in the marketplace for a plant-derived gelling agent. A variety of such agents exist, but one of the best known is carrageenan, which is found in abundance in seaweed. Carrageenans are polysaccharides, and specifically galactans, comprising alternating copolymers of $\alpha(1\rightarrow3)$-D-galactose and $\beta(1\rightarrow4)$-3,6-anhydro-D-galactose units. Several members of the carrageenan family are known, differing in their amounts of sulfate ester and/or other substituent groups, including iota-carrageenan, kappa-carrageenan and lambda-carrageenan, of which only iota- and kappa-carrageenans have gelling properties.

A general formula for carrageenan is disclosed by NIJENHUIS, K. in *Advanced Polymer Science* 130, 203–218, (1997) (hereinafter NIJENHUIS), which is hereby expressly incorporated by reference as though set forth in full herein. STORTZ, C. A. and CEREZO, A. S. describe in *Carbohydrate Research* 145 (1986), 219–235 (hereinafter STORTZ and CEREZO, which is expressly incorporated by reference as though set forth in full herein), the different members of the carrageenan family by their idealized repeating units:

| Carrageenan | 3-linked residue | 4-linked residue |
| --- | --- | --- |
| Beta | Beta-D-galactopyranose 4-sulfate | 3,6-anhydro-alpha-D-galactopyranose |
| Kappa | Beta-D-galactopyranose 4-sulfate | 3,6-anhydro-alpha-D-galactopyranose |
| Iota | Beta-D-galactopyranose 4-sulfate | 3,6-anhydro-alpha-D-galactopyranose 2-sulfate |
| Mu | Beta-D-galactopyranose 4-sulfate | Alpha-D-galactopyranose 6-sulfate |
| Nu | Beta-D-galactopyranose 4-sulfate | Alpha-D-galactopyranose 2,6-disulfate |
| Lambda | Beta-D-galactopyranose 2-sulfate (70%) and Beta-D-galactopyranose (30%) | Alpha-D-galactopyranose 2,6-disulfate |
| Theta | Beta-D-galactopyranose 2-sulfate | 3,6-anhydro-alpha-D-galactopyranose 2-sulfate |
| Xi | Beta-D-galactopyranose 2-sulfate | Alpha-D-galactopyranose 2-sulfate |

It is generally known that the gelling ability of carrageenan is influenced by alkali treatment, through which a 3,6-anhydro bond is formed via a de-esterification of the C-6 sulfate esters present, thus causing a decrease in water solubility. The viscoelastic behavior of carrageenans is affected not only by alkali treatment, but by electrolyte concentration, carrageenan type, protein interaction, molecular weight and concentration of the carrageenan, as well as temperature. A general discussion of the qualities of carrageenans is presented in Chapter 3 of *Thickening and Gellin Agents for Food, Second Edition* (Imeson, ed., Chapman & Hall, N.Y. 1997) (hereinafter IMESON), and in Chapter 7 of *Industrial Gums: Polysaccharides and Their Derivatives, Third Edition* (Whistler and BeMiller, eds., Academic Press, San Diego 1993) (hereinafter WHISTLER). IMESON and WHISTLER are hereby expressly incorporated by reference as though set forth in full herein. Thus, the complex mechanisms underlying the viscoelastic behavior of a particular carrageenan makes it difficult to predict the properties thereof. Moreover, viscoelastic behavior is sometimes not predictive of subjective consumer preference.

Presently, there is room for improvement in commercially available carrageenans. For example, temperature sensitivity of currently available carrageenans is somewhat inadequate, i.e., while the carrageenans may have a desirable elastic texture at temperatures below 15 to 20° C., they are gummy at temperatures prevailing in the mouth. Ideally, the carrageenans should show viscous or plastic characteristics in order to be useful as gelling agents in, for example, water desserts. Furthermore, the present commercially available carrageenans are characterized by forming relatively rigid gel structures, which do not show the desired "ring," which is desirable in some applications, such as water desserts and milk desserts. Additionally, the presently available carrageenans are not completely satisfactory from a subjective consumer point of view.

A number of processes exist for the extraction and modification of carrageenans, each contributing in different ways to the qualities of the finished product. Examples include Ciancia, M. et al. *Carbohydrate Polymers* 32, (1997), 293–295, "Alkaline modification of carrageenans. Part III. Use of mild alkaline media and high ionic strengths," (hereinafter CIANCIA) in which alkaline modification of carrageenans by the use of sodium carbonate at pH-values of at least 12 is presented. CIANCIA is hereby expressly incorporated by reference as though set forth in full herein.

U.S. Pat. No. 2,624,727, to LEGLOAHEC ("LEGLOAHEC"), is an early example of a method for extracting carrageenan from seaweeds. LEGLOAHEC emphasizes the need for having cations present in the extraction step for cation exchange.

U.S. Pat. No. 3,094,517, to STANLEY ("STANLEY") is directed to a process for extracting carrageenans from seaweed. STANLEY presents an extensive discussion of the role of alkaline hydrolysis in the extraction procedure. Calcium hydroxide is described as preferable for the extraction procedure.

U.S. Pat. No. 3,176,003, to STANICOFF is directed to a process for extracting kappa and lambda carrageenans from seaweed using hydroxide salts.

U.S. Pat. No. 3,342,612, to FOSTER et al. ("FOSTER") discloses extractives derived from sea plants and their recovery and treatment, as well as compositions comprising such extractives including aqueous gels. In particular, FOSTER discloses that an extractive may be obtained from *Eucheuma spinosum* and *Agarchiella tenera* and emphasizes that, as compared to conventional processes, the amount of calcium hydroxide is important, as is the temperature. Optimally, the quantity of calcium hydroxide is disclosed to be about 7% by weight, based on the weight of the dry sea plant. The preferred temperature is disclosed to be from about 90°–100° C.

U.S. Pat. No. 3,907,770, to STRONG is directed to a process for extracting carrageenan from seaweed using a process which includes digesting at elevated temperatures a mixture of seaweed with water and an alkaline earth metal hydroxide or an alkali metal hydroxide. The seaweed content is disclosed to be equal to at least about 9% by weight, based on the dry weight of the seaweed.

U.S. Pat. No. 5,502,179, to LARSEN discloses a carrageenan product which is disclosed to be useful as an emulsifier and for thickening or gelling aqueous systems. The product is apparently made by subjecting a carrageenan-containing material in which 6-sulfated galactose units have been converted into 3,6-anhydro galactose units to a shear stress treatment.

In the alkaline extraction of carrageenan from seaweed, nu carrageenan, which is present in the seaweed, is converted to iota carrageenan, which is also present in the seaweed. This conversion is generally seen as desirable when iota carrageenan is the desired end product. This reaction is described in WHISTLER and shown diagrammatically as follows:

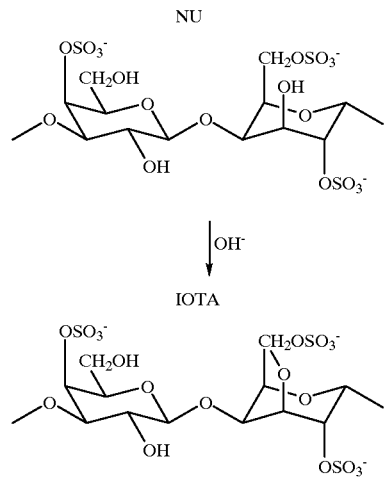

However, none of the presently available carrageenans provide the desired combination of elastic characteristics at temperatures below room temperature and plastic and/or viscous characteristics at mouth and body temperatures.

SUMMARY OF THE INVENTION

In view of the foregoing, the present invention is directed to carrageenan compositions.

The present invention is further directed to carrageenan compositions exhibiting superior rheological behavior and desirable organoleptic qualities, when used in concentrations which are desirable.

The present invention is further directed to carrageenan compositions which exhibit a pronounced temperature sensitivity in the temperature range 5 to 25° C.

The present invention is further directed to gelling agents which are vegetable based.

The present invention is fuither directed to methods of producing carrageenan compositions The present invention is further directed to methods of producing carrageenan compositions which exhibit superior rheological behavior and desirable organoleptic qualities.

The present invention is further directed to methods of producing carrageenan compositions, which methods exhibit improved production efficiency.

The present invention is still further directed to compositions comprising carrageenan compositions which exhibit superior rheological behavior and desirable organoleptic qualities.

The present invention is directed to the use of carrageenan compositions in foods, pharmaceuticals and personal care products and the like.

These and other aspects of the present invention are achieved by a composition comprising from about 79 mol % to about 95 mol % iota carrageenan and from about 0.1 mol % to about 10 mol % nu carrageenan, when measured using $^{13}$C-NMR. Preferably, the composition comprises from about 82 mol % to about 92 mol % iota carrageenan, and most preferably, from about 85 mol % to about 89 mol % iota carrageenan, when measured using $^{13}$C-NMR. Preferably, the composition comprises from about 3 mol % to about 8.5 mol % nu carrageenan, and most preferably from about 5 mol % to about 7 mol % nu carrageenan, when measured using $^{13}$C-NMR. Preferably, the composition exhibits a molecular weight of higher than about 600 kD, and more preferably from about 600 kD to about 1,000 kD, when measured with size exclusion chromatography, and as compared to poly(ethylene oxide) standards.

The composition may be used in combination with a gelling agent comprising at least one member selected from the group consisting of low-methoxyl pectin, locust bean gum, farcellaran, agar, gellan gum, kappa carrageenan, gelatin, xanthan gum, alginate, and combinations thereof. Preferably, the gelling agent comprises kappa carrageenan.

Preferably, the composition exhibits a melting point of less than 60° C., more preferably from about 45° C. to less than 60° C., even more preferably from about 45° C. to about 55° C., and most preferably from about 45° C. to about 50° C., in a 1.2 wt % aqueous gel. Preferably, the composition exhibits an elastic modulus, G'—1 Hz at 5° C., of greater than about 200 Pa, more preferably from greater than about 200 Pa to about 400 Pa, more preferably from about 250 Pa to about 350 Pa, even more preferably from about 250 Pa to about 325 Pa, and most preferably from about 250 Pa to about 300 Pa, in a 1.2 wt % aqueous gel. Preferably, the composition exhibits an elastic modulus, G'—1 Hz at 25° C., of less than about 200 Pa, more preferably from about 80 Pa to less than about 200 Pa, more preferably from about 80 Pa to about 180 Pa, even more preferably from about 80 Pa to about 160 Pa, and most preferably from about 80 Pa to about 120 Pa, in a 1.2 wt % aqueous gel. Preferably, the composition exhibits loss of elastic modulus, %ΔG' between 5° C. and 25° C., of greater than about 20%, more preferably from greater than about 20% to about 80%, more preferably from about 35% to about 80%, even more preferably from about 50% to about 80%, and most preferably from about 55% to about 80%, in a 1.2 wt % aqueous gel. Preferably, the composition exhibits a viscous modulus, G"—0.2 Hz at 5° C., of greater than about 5 Pa, more preferably from greater than about 5 Pa to about 25 Pa, more preferably from about 10 Pa to about 25 Pa, even more preferably from about 15 Pa to about 25 Pa, and most preferably from about 20 Pa to about 25 Pa, in a 1.2 wt % aqueous gel.

Preferably, the composition exhibits a break strength (in grams of force), at 5° C., of from about 200 to about 600 g, more preferably from about 350 to about 600 g, and most preferably from about 500 to about 600 g, in a 1.2 wt % aqueous gel. Preferably, the composition exhibits a break strength, at 25° C., of from about 110 to about 160 g, more preferably from about 110 to about 145 g, and most preferably from about 110 to about 130 g, in a 1.2 wt % aqueous gel. Preferably, the composition exhibits change in break strength, from 5° C. to 25° C., of from about 40 to about 80%, more preferably from about 50 to about 80%, and most preferably from about 60 to about 80%, in a 1.2 wt % aqueous gel.

Preferably, the composition exhibits gel strength (in grams of force), at a 2 mm compression distance, at 5° C., of from about 10 to about 25 g, more preferably from about 15 to about 25 g, and most preferably from about 20 to about 25 g, in a 1.2 wt % aqueous gel. Preferably, the composition exhibits gel strength, 2 mm, at 25° C., of from about 7 to about 15 g, more preferably from about 7 to about 12 g, and most preferably from about 7 to about 9 g, in a 1.2 wt % aqueous gel. Preferably, the composition exhibits change in gel strength, 2 mm, from 5° C. to 25° C., of from about 20 to about 60%, more preferably from about 35 to about 60%, and most preferably from about 50 to about 60%, in a 1.2 wt % aqueous gel.

Preferably, the composition exhibits gel strength (in grams of force), at a 15 mm compression distance, at 5° C., of from about 100 to about 300 g, more preferably from about 150 to about 300 g, and most preferably from about 200 to about 300 g, in a 1.2 wt % aqueous gel. Preferably, the composition exhibits gel strength, 15 mm, at 25° C., of from about 60 to about 90 g, more preferably from about 60 to about 80 g, and most preferably from about 60 to about 70 g, in a 1.2 wt % aqueous gel. Preferably, the composition exhibits change in gel strength, 15 mm, from 5° C. to 25° C., of from about 20 to about 60%, more preferably from about 35 to about 60%, and most preferably from about 50 to about 60%, in a 1.2 wt % aqueous gel.

Preferably, the composition exhibits break distance, at 5° C, of from about 20 to about 30 mm, more preferably from about 25 to about 30 mm, and most preferably from about 28 to about 30 mm, in a 1.2 wt % aqueous gel. Preferably, the composition exhibits break distance, at 25° C., of from about 20 to about 26 mm, more preferably from about 20 to about 25 mm, and most preferably from about 20 to 24 mm, in a 1.2 wt % aqueous gel. Preferably, the composition exhibits change in break distance, from 5° C. to 25° C., of from about 5 to about 20%, more preferably from about 10 to about 20%, and most preferably from about 15 to about 20%, in a 1.2 wt % aqueous gel.

Preferably, the composition exhibits negative force-time area, at 5° C., of from about −1500 to about −4000 g·sec, more preferably from about −2500 to about −4000 g·sec, and most preferably from about −3500 to about −4000 g·sec, in a 1.2 wt % aqueous gel. Preferably, the composition exhibits negative area, at 25° C., of from about −900 to about −1200 g·sec, more preferably from about −900 to about −1100 g·sec, and most preferably from about −900 to about −1000 g·sec, in a 1.2 wt % aqueous gel. Preferably, the composition exhibits change in negative area, from 5° C. to 25° C., of from about 50 to about 80%, more preferably from about 60 to about 80%, and most preferably from about 70 to about 80%, in a 1.2 wt % aqueous gel.

The present invention is further achieved by the provision of compositions comprising iota carrageenan and nu carrageenan, wherein the molar ratio of iota carrageenan to nu carrageenan is greater than about 6:1; exhibiting loss of elastic modulus, %ΔG' between 5° C. and 25° C., of greater than about 20%, in a 1.2 wt % aqueous gel; and exhibiting change in gel strength, 2 mm, from 5° C. to 25° C., of greater than about 20%, in a 1.2 wt % aqueous gel. Preferably, the molar ratio of iota carrageenan to nu carrageenan is from greater than about 6:1 to about 1000:1, more preferably, from about 8:1 to about 100:1, even more preferably, from about 9:1 to about 25:1, and most preferably, from about 10:1 to about 20:1.

The present invention is further achieved by the provision of a composition comprising from about 79 mol % to about 95 mol % iota carrageenan and from about 0.1 mol % to about 10 mol % nu carrageenan, when measured using $^{13}$C-NMR, exhibiting elastic modulus, G'—1 Hz at 5° C., of greater than about 200 Pa, elastic modulus, G'—1 Hz at 25° C., of less than about 200 Pa, viscous modulus, G"—0.2 Hz at 5° C., of greater than about 5 Pa, and melting point of less than 60° C., in a 1.2 wt % aqueous gel. Preferably, the composition exhibits a molecular weight of greater than about 600 kD when measured with size exclusion chromatography, as compared to poly(ethylene oxide) standards.

The present invention is still further achieved by the provision of a method of producing a carrageenan composition comprising contacting carrageenan-containing material with a basic monovalent cationic solution under time, temperature, pH, and ionic conditions, to obtain carrageenan composition having from about 79 mol % to about 95 mol % iota carrageenan and from about 0.1 mol % to about 10 mol % nu carrageenan, when measured using $^{13}$C-NMR. Preferably, the method comprises contacting carrageenan-containing material with a basic monovalent cationic solution for a period of from about 10 minutes to about 200 minutes, at a temperature of from about 65° C. to about 135° C., wherein the basic monovalent cationic solution has a pH of from about 8 to about 11.5, and a concentration of carbonate or bicarbonate of from about 0.05 M to about 0.5 M, to obtain carrageenan composition having from about 79 mol % to about 95 mol % iota carrageenan and from about 0.1 mol % to about 10 mol % nu carrageenan, when measured using $^{13}$C-NMR. More preferably, the method comprises contacting carrageenan-containing material with a basic monovalent cationic solution for a period of from about 20 minutes to about 120 minutes, at a temperature of from about 95° C. to about 125° C., wherein the basic monovalent cationic solution has a pH of from about 8.5 to about 10.5, and a concentration of carbonate or bicarbonate of from about 0.06 M to about 0.4 M, to obtain carrageenan composition having from about 79 mol % to about 95 mol % iota carrageenan and from about 0.1 mol % to about 10 mol % nu carrageenan, when measured using $^{13}$C-NMR. Even more preferably, the method comprises contacting carrageenan-containing material with a basic monovalent cationic solution for a period of from about 30 minutes to about 60 minutes, at a temperature of from about 95° C. to about 125° C., wherein the basic monovalent cationic solution has a pH of from about 9 to about 10, and a concentration of carbonate or bicarbonate of from about 0.07 M to about 0.3 M, to obtain carrageenan composition having from about 79 mol % to about 95 mol % iota carrageenan and from about 0.1 mol % to about 10 mol % nu carrageenan, when measured using $^{13}$C-NMR. Most preferably, the method comprises contacting carrageenan-containing material with a basic monovalent cationic solution for a period of from about 30 minutes to about 60 minutes, at a temperature of from about 110° C. to about 121° C., wherein the basic monovalent cationic solution has a pH of from about 9 to about 10, and a concentration of carbonate or bicarbonate of from about 0.07 M to about 0.3 M, to obtain carrageenan composition having from about 79 mol % to about 95 mol % iota carrageenan and from about 0.1 mol % to about 10 mol % nu carrageenan, when measured using $^{13}$C-NMR.

The basic monovalent cationic solution may comprise at least one member selected from the group consisting of sodium carbonate, potassium carbonate, sodium bicarbonate, potassium bicarbonate, ammonium carbonate, and combinations thereof. Preferably, the solution comprises carbonate or bicarbonate salt of monovalent cation in an amount which is from about 5% to about 20%, more preferably from about 5% to about 15%, and most preferably from about 5% to about 11%, of the dry weight of the starting material.

Also provided is a method of producing a carrageenan composition comprising treating carrageenan-containing material with a basic monovalent cationic solution under time, temperature, pH, and ionic conditions, to obtain carrageenan composition exhibiting elastic modulus, G'—1 Hz at 5° C., of greater than about 200 Pa, elastic modulus, G'—1 Hz at 25° C., of less than about 200 Pa, viscous modulus, G"—0.2 Hz at 5° C., of greater than about 5 Pa, and melting point of less than 60° C., in a 1.2 wt % aqueous gel.

Also provided is a method of producing a carrageenan composition comprising treating carrageenan-containing material with solution having a pH of from about 8 to about 11.5, at a temperature of from about 65° C. to about 90° C., for a period of from about 10 minutes to about 200 minutes, to produce from about 79 mol % to about 95 mol % iota carrageenan and from about 0.1 mol % to about 10 mol % nu carrageenan, when measured using $^{13}$C-NMR; separating treated starting material from the solution; adjusting the pH of the starting material; washing treated starting material; and drying treated starting material.

The present invention is further achieved by the provision of a foodstuffs, pharmaceutical preparations, cosmetics, household products, and personal care products, comprising any of the aforementioned carrageenan compositions. The foodstuffs preferably comprise from about 0.4 to about 2.6 wt %, and more preferably from about 0.6 to 1.3 wt % carrageenan composition. Such foodstuffs include water desserts, milk desserts, or processed meat products. Pharmaceutical preparations include oral, topical, or veterinary. Personal care products include toothpaste and skin care preparations. Household products include air-freshener gels or cleaning gels.

BRIEF DESCRIPTION OF THE DRAWINGS

The foregoing and other features and advantages of the invention will be apparent from the following more particular description of the preferred embodiments, as illustrated in the accompanying drawings, in which reference characters refer to the same, or like, parts throughout the various views, and wherein.

DETAILED DESCRIPTION OF PREFERRED EMBODIMENTS OF THE INVENTION

Figure 1A:
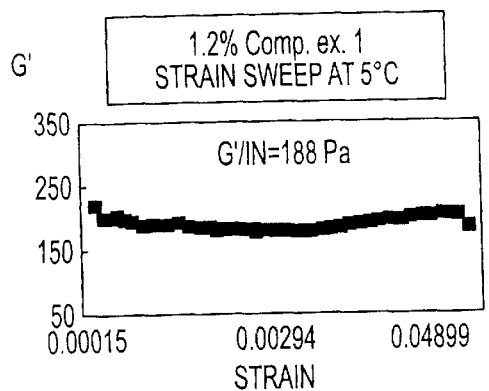
FIGS. 1A and 1B show strain sweeps from comparative carrageenan compositions, at 5° C. and 25° C., respectively.
Figure 1B:
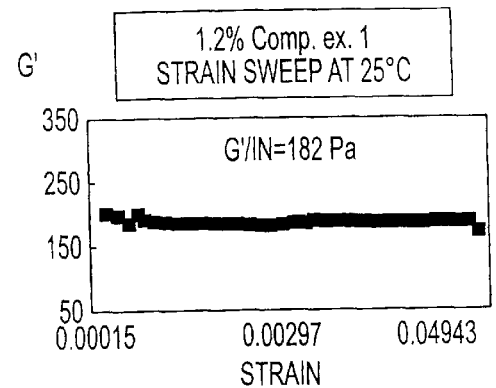
Figure 1C:
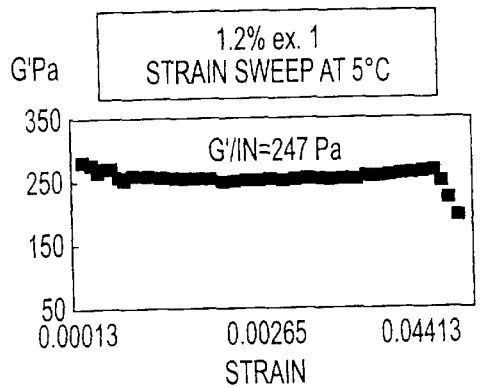
FIGS. 1C and 1D show strain sweeps from carrageenan according to the invention, at 5° C. and 25° C., respectively.
Figure 1D:
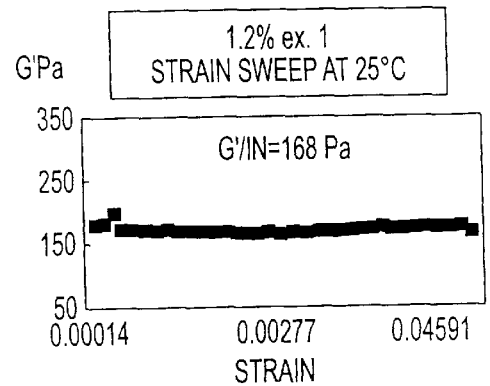
Figure 1E:
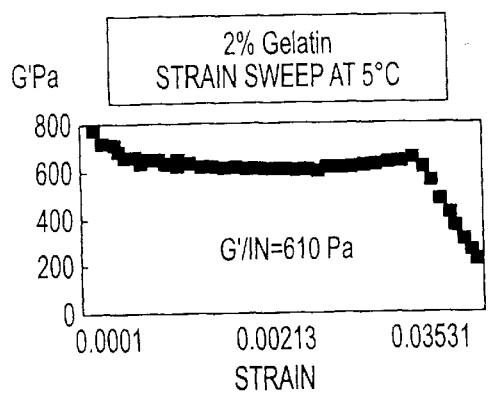
FIGS. 1E and 1F show strain sweeps from gelatin compositions, at 5° C. and 25° C., respectively.
Figure 1F:
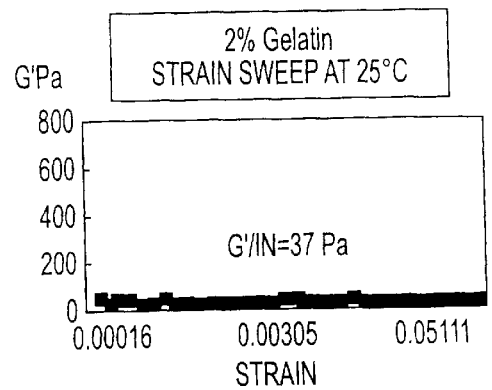

The present invention, amongst other features, is directed to carrageenan compositions which exhibit desirable physical qualities. Specifically, gels prepared using carrageenan compositions of the present invention exhibit desirable firmness at lower temperatures, yet desirable softness at higher temperatures. These qualities make carrageenan compositions of the present invention especially desirable for use in products such as foodstuffs, pharmaceuticals, cosmetics, and other similar products.

In particular, the present invention is directed to carrageenan compositions which exhibit superior rheological behavior and/or textural qualities and/or organoleptic qualities. As used herein, rheological, and textural qualities are in reference to a gel having the following components (in parts by weight, with the total weight comprising 100 parts):15.00 parts by weight fine mesh (30 mesh) sugar (sucrose); 0.30 parts by weight tri-potassium citrate, monohydrate; 0.15 parts by weight calcium chloride, dihydrate; 0.20 parts by weight citric acid, anhydrous; 1.2 parts by weight carrageenan (neat); and 83.15 parts by weight demineralized water. The dry ingredients are weighed and mixed well and boiling water is added while stirring vigorously to form a solution. The solution is allowed to cool to form a gel. The properties can be tested either during or after gelation.

The rheological parameters which are of interest include 1) elastic modulus, G'—1 Hz at 5° C. ("gel strength"), 2) elastic modulus, G'—1 Hz at 25° C. ("gumminess"), 3) loss of elastic modulus, %ΔG' between 5° C. and 25° C. ("softening"), and 4) viscous modulus, G"—0.2 Hz, 5° C. ("ring").

The elastic modulus, G', indicates the solid behavior of a gel. The elastic moduli measured at 5° C. can be referred to as "gel strength." Carrageenan compositions of the present invention, in a 1.2 wt % aqueous gel, exhibit gel strength elastic moduli (G'—1 Hz at 5° C.) of greater than about 200 Pa, more preferably, from greater than about 200 to about 400 Pa, more preferably from about 250 to about 350 Pa, even more preferably from about 250 to about 325 Pa, and most preferably from about 250 to about 300 Pa.

The elastic modulus measured at 25° C. can be referred to as "gumminess." Carrageenan compositions of the present invention, in a 1.2 wt % aqueous gel, exhibit gumminess elastic moduli (G'—1 Hz at 25° C.) of less than about 200 Pa, more preferably, from about 80 to less than about 200 Pa, more preferably from about 80 to about 180 Pa, even more preferably from about 80 to about 160 Pa, and most preferably from about 80 to about 120 Pa.

The loss in gel strength, measured as a function of temperature, indicates the extent to which the gel is perceived to liquefy on warming, and is thus a measure of the watery feel or fluidity in the mouth. Gel strength loss is defined herein as the loss in elastic modulus in the temperature interval from 5° C. to 25° C.

$$\text{Thus, gel strength loss }\% = \left[\frac{G'(5°\text{C.}) - G'(25°\text{C.})}{G'(5°\text{C.})}\right] \times 100$$

Carrageenan compositions of the present invention, in a 1.2 wt % aqueous gel, exhibit loss of elastic moduli (%ΔG' between 5° C. and 25° C.) of greater than about 20%, more preferably from greater than about 20% to about 80%, more preferably from about 35% to about 80%, even more preferably from about 50% to about 80%, and most preferably from about 55% to about 80%.

The viscous modulus, G"—0.2 Hz, 5° C., indicates the liquid behavior of the gel, and can be referred to as "ring." Carrageenan compositions of the present invention, in a 1.2 wt % aqueous gel, exhibit viscous moduli (G"—0.2 Hz, 5° C.) of greater than about 5 Pa, more preferably from greater than about 5 Pa to about 25 Pa, more preferably from about 10 to about 25 Pa, even more preferably from about 15 to about 25 Pa, and most preferably from about 20 to about 25 Pa.

Additionally, carrageenan compositions of the present invention can be characterized by melting point. Carrageenan compositions of the present invention, in a 1.2 wt % aqueous gel, exhibit a melting point of less than 60° C., more preferably from about 45° C. to less than 60° C., even more preferably from about 45° C. to about 55° C., and most preferably from about 45° C. to about 50° C.

Additionally, carrageenan compositions of the present invention exhibit desirable textural properties. In particular, carrageenan compositions of the present invention exhibit desirable break strength, gel strength, break time, and negative area, all of which can be measured on a texture analyzer, such as, for example, a TA-XT2 Texture Analyzer manufactured by Stable Micro Systems (Godalming, Surrey, UK).

Break strength (BS) is the force (in grams) required to compress the gel to the point of break with a one inch diameter probe. Carrageenan compositions of the present invention, in a 1.2 wt % aqueous gel, exhibit break strength, at 5° C., of from about 200 to about 600 g, more preferably from about 350 to about 600 g, and most preferably from about 500 to about 600. Carrageenan compositions of the present invention, in a 1.2 wt % aqueous gel, exhibit break strengths at 25° C. of from about 110 to about 160 g, more preferably from about 110 to about 145 g, and most preferably from about 110 to about 130 g. Carrageenan compositions of the present invention, in a 1.2 wt % aqueous gel, exhibit change in break strength from 5° C. to 25° C. of from about 40 to about 80%, more preferably from about 50 to about 80%, and most preferably from about 60 to about 80%.

Gel strength (GS) is the force (in grams) required to compress the gel to a depth of 2mm and 15 mm with a one inch diameter probe. Carrageenan compositions of the present invention in, a 1.2 wt % aqueous gel, exhibit gel strength, 2 mm, at 5° C., of from about 10 to about 25 g, more preferably from about 15 to about 25 g, and most preferably from about 20 to about 25 g. Carrageenan compositions of the present invention, in a 1.2 wt % aqueous gel, exhibit gel strength, 2 mm, at 25° C., of from about 7 to about 15 g, more preferably from about 7 to about 12 g, and most preferably from about 7 to about 9 g. Carrageenan compositions of the present invention, in a 1.2 wt % aqueous gel, exhibit change in gel strength, 2 mm, from 5° C. to 25° C., of greater than about 20%, preferably from greater than about 20% to about 60%, more preferably from about 35 to about 60%, and most preferably from about 50 to about 60%.

Carrageenan compositions of the present invention, in a 1.2 wt % aqueous gel, exhibit gel strength, 15 mm, at 5° C., of from about 100 to about 300 g, more preferably from about 150 to about 300 g, and most preferably from about 200 to about 300 g. Carrageenan compositions of the present invention, in a 1.2 wt % aqueous gel, exhibit gel strength, 15 mm, at 25° C., of from about 60 to about 90 g, more preferably from about 60 to about 80 g, and most preferably from about 60 to about 70 g. Carrageenan compositions of the present invention, in a 1.2 wt % aqueous gel, exhibit change in gel strength, 15 mm, from 5° C. to 25° C., of from about 20 to about 60%, more preferably from about 35 to about 60%, and most preferably from about 50 to about 60%.

Break distance (BD) is the distance (in mm) the one inch diameter probe travels to break a gel. Break distance is measured with a probe speed of 1 mm/sec. Carrageenan compositions of the present invention, in a 1.2 wt % aqueous gel, can exhibit break distance, at 5° C., of from about 20 to about 30 mm. Carrageenan compositions of the present invention, in a 1.2 wt % aqueous gel, can exhibit break distance, at 25° C., of from about 20 to about 26 mm. Carrageenan compositions of the present invention, in a 1.2 wt % aqueous gel, can exhibit change in break distance, from 5° C. to 25° C., of from about 5 to about 20%.

Negative area (NA) is the area below the x-axis when a plot of force as a function of compression distance is plotted as the probe is withdrawn from the sample. Carrageenan compositions of the present invention, in a 1.2 wt % aqueous gel, exhibit negative area, at 5° C., of from about −1500 to about −4000 g·sec, more preferably from about −2500 to about −4000 g·sec, and most preferably from about −3500 to about −4000 g·sec. Carrageenan compositions of the present invention, in a 1.2 wt % aqueous gel, exhibit negative area, at 25° C., of from about −900 to about −1200 g·sec, more preferably from about −900 to about −1100 g·sec, and most preferably from about −900 to about 1000 g·sec. Carrageenan compositions of the present invention, in a 1.2 wt % aqueous gel, exhibit change in negative area, from 5° C. to 25° C., of from about 50 to about 80%, more preferably from about 60 to about 80%, and most preferably from about 70 to about 80%.

Each of the rheological, textural, and organoleptic qualities discussed herein is simply a component of the overall desirable physical behavior of carrageenan compositions of the present invention. Preferably, carrageenan compositions of the present invention exhibit all of the aforementioned desirable qualities. However, carrageenan compositions of the present invention may exhibit one or more of these preferred properties. For example, carrageenan compositions produced in accordance with the present invention may exhibit an elastic modulus, G'—1 Hz at 5° C. ("gel strength"), elastic modulus, G'—1 Hz at 25° C. ("gumminess"), break strength, and gel strength, with preferred values, yet may exhibit a melting point which is higher than is preferable. As another example, a carrageenan composition produced in accordance with the present invention may exhibit a preferred melting point, yet fall outside any or all of the preferred ranges for elastic and viscous moduli and negative area. In other words, carrageenan compositions produced in accordance with the present invention can be characterized in terms of their physical qualities, yet the physical qualities are not necessarily determinative of carrageenan compositions produced in accordance with the present invention. Most preferably, however, carrageenan compositions of the present invention exhibit all of the preferred physical qualities.

As discussed above, a variety of carrageenans have been identified, each characterized by their idealized repeating units, including beta, kappa, iota, mu, nu, lambda, theta, and xi carrageenans. Carrageenan compositions of the present invention comprise at least nu and iota carrageenans. Carrageenan compositions of the present invention comprise iota carrageenan in amounts of from about 79 mol % to about 95 mol %, more preferably from about 82 mol % to about 92 mol %, and most preferably from about 85 mol % to about 89 mol %. Carrageenan compositions of the present invention comprise nu carrageenan in amounts of from about 0.1 mol % to about 10 mol %, more preferably from about 3 mol % to about 8.5 mol %, and most preferably from about 5 mol % to about 7 mol %.

The levels of carrageenan constituents in a carrageenan composition can be measured in a number of different manners; however, most preferred for measurement of carrageenan components is NMR, and values presented herein for carrageenan compositions defining the invention are those based on NMR measurements. Additionally, chemical analysis and IR measurements may also be used to determine the levels of the carrageenan constituents. Details of these procedures are presented below under "Test Methods," and IR measurements, in addition to NMR measurements, are included in some Examples.

Carrageenan compositions of the present invention may also be characterized by other qualities, including molecular weight. Molecular weight is preferably determined using size exclusion chromatography (SEC) using poly(ethylene oxide) (PEO) standards, and molecular weight values presented herein are those determined using SEC with PEO standards. Details of these procedures are presented below under "Test Methods." The molecular weight of the carrageenan components of the carrageenan compositions of the present invention preferably exceed about 600 kilodaltons (kD), and are more preferably between about 600 kD and about 1,000 kD.

The present invention also relates to compositions comprising a combination of carrageenan compositions as defined above and at least one other component. For example, additional components can comprise salts, sugars, colorants, flavorings, chelators, or may comprise another gelling agent. This kind of combination may be used to tailor the gelling properties of the mixture, and thereby change the qualities of the end product. In this manner, a combination of the novel carrageenan composition according to the present invention and another gelling agent, such as a kappa carrageenan results in a product which can be tailored precisely to specific applications. The additional gelling agent may be selected from a variety of gelling agents, and preferably comprises a member selected from the group consisting of low-methoxyl pectin, locust bean gum, faircellaran, agar, gellan gum, kappa carrageenan, gelatin, xanthan gum, alginate, and mixtures thereof, but is most preferably a kappa carrageenan or locust bean gum.

The present invention also relates to compositions comprising iota carrageenan and nu carrageenan in molar ratios wherein the ratio of iota carrageenan to nu carrageenan is greater than about 6:1. Preferably the ratio of iota carrageenan to nu carrageenan ranges from greater than about 6:1 to about 1000:1, more preferably from about 8:1 to about 100:1, even more preferably from about 9:1 to about 25:1, and most preferably from about 10:1 to about 20:1.

Carrageenan compositions of the present invention may be obtained from a variety of sources. Preferably, carrageenan compositions of the present invention are obtained from seaweed of the order Gigartinales, preferably from the genera Eucheuma, Agardhiella, Callihlepharis, Gymnogongrus, Uncinanum, Isiforme or Phyllophora, most preferably from the species *Eucheuma deuticulaium*, also know as *Eucheuma spinosum*. Carrageenans made from these seaweeds are characterized by forming gels that show very little syneresis, are freeze-thaw stable, cohesive, soft, rubbery and show a considerable yield point at low concentrations.

Processes for production of carrageenan compositions of the present invention are not particularly limited, as long as a product which exhibits the desired characteristics is obtained. Preferably, processes for production of carrageenan compositions of the present invention comprise extraction from a carrageenan-containing substrate, or starting material. As noted above, the starting material is preferably seaweed, and is most preferably *Eucheuma spinosum*. In addition to extraction, processes of the present invention may further comprise additional processes, including but not limited to, ion exchange, filtration, neutralization or pH adjustment, precipitation, drying, and/or grinding.

With regard to the extraction procedure, it has been found that the time, temperature, pH, and ionic concentration each effect the product of the extraction. Without wishing to be bound by theory, it is believed that by carrying out the extraction at lower pH values than traditionally applied, e.g., closer to neutral pH, a less complete alkali modification of the carrageenan takes place, that is, fewer galactose units with sulphate esters are converted to 3,6 anhydro-galactose (conversion of iota carrageenan to nu carrageenan). It is believed that this leads to fewer junction zones and thus, a less rigid gel structure. For example, when extracting red seaweed at a pH above about 12, from about 98% to about 100% of the 6-sulfate ester galactose units are converted to 3,6 anhydro-galactose, measured by chemical analysis, whereas this conversion is only about 76% to about 82% when extraction is carried out at neutral pH. Thus, at higher pH, more iota carrageenan is converted to nu, and at neutral pH, the conversion is less. However, when milder alkalis, such as sodium carbonate, are used in the extraction to produce a lower pH, the conversion leaves iota carrageenan concentrations in ranges of the present invention.

Additionally, at lower temperatures, the conversion of iota to nu proceeds more slowly, and the converse is true as temperature increases. Another factor which is believed to affect the rate of conversion is the presence or absence of polyvalent cations. Thus, by carefully manipulating the various factors, including time, temperature, pH, and ionic characteristics, the preferred ratio of iota and nu carrageenan can be obtained.

It has been found that the following extraction procedure is superior for producing a carrageenan composition exhibiting the desired combination of nu and iota forms. Extraction in accordance with the present invention comprises heating a carrageenan-containing starting material in a solution at a mildly alkaline pH. The pH of the extraction is basic, and is preferably from about 8 to about 11.5, more preferably from about 8.5 to about 10.5, and most preferably from about 9 to about 10. Because the temperature can have an effect on the pH, the pH should be determined at operating temperature. Heating is preferably performed at a temperature of from about 65° C. to about 135° C., more preferably from about 95° C. to about 125° C., and most preferably from about 110° C. to about 121° C. The extraction time will vary, depending on the temperature and pH, but preferably ranges from about 10 minutes to about 200 minutes, more preferably, from about 20 minutes to about 120 minutes, and most preferably, from about 30 minutes to about 60 minutes.

The solution at mildly alkaline pH comprises a monovalent cationic solution. Preferably, polyvalent cation is present in no more than trace amounts. Preferably, the solution is substantially free of polyvalent cation, such as divalent cation. Thus, preferably, polyvalent cation is present at less than about 5 mg/g of carrageenan-containing starting material, more preferably less than 3 mg/g, even more preferably less than 1 mg/g, and most preferably less than 0.75 mg/g. Preferably, polyvalent cations are not added to the solution, and the only polycations present are the trace amounts present from the starting materials.

The solution at mildly alkaline pH preferably comprises carbonate and/or bicarbonate salt of monovalent cation. Preferably the carbonate or bicarbonate salt comprises sodium carbonate, potassium carbonate, sodium bicarbonate, potassium bicarbonate, and/or ammonium carbonate. The concentration of the carbonate or bicarbonate is preferably from about 0.05 M to about 0.5 M, more preferably, from about 0.06 M to about 0.4 M, and is most preferably from about 0.07 M to about 0.3 M. In relation to the dry weight of the starting material, for example seaweed, the carbonate or bicarbonate is preferably present in amounts of from about 5% to about 20%, more preferably from about 5% to about 15%, and most preferably from about 5% to about 11%, of the dry weight of the starting material.

Following extraction, the resulting mixture is preferably neutralized. The manner in which the neutralization is effected will vary, depending on the pH of the mixture following extraction. Specifically, the neutralization may be performed by washing with water, or by addition of acid, including any acid, either organic or inorganic, including but not limited to, acetic acid, citric acid, hydrochloric acid (HCl), sulfuric acid ($H_2SO_4$), phosphoric acid ($H_2PO_4$), nitric acid ($HNO_3$), and carbonic acid ($H_2CO_3$). The neutralization may be performed by bubbling $CO_2$ through the mixture. Preferably, the pH of the mixture following neutralization is from about 7 to about 9.5.

After neutralization, the extracted carrageenan may be separated from the undissolved seaweed residue. This may be performed in a variety of manners. The filtration may be performed by methods including, but not limited to, vacuum filtration, pressure filtration or centrifugation. To aid in filtration, paper pulp, diatomaceous earth or other filtering aids may be added to the extraction mixture prior to filtration in an amount sufficient to obtain a clear extract.

After the carrageenan has been separated from the residual seaweed, the carrageenan may be isolated by drying or precipitation from the solvent. This may be performed in a variety of manners, including but not limited to, addition of organic solvent. Preferably, the organic solvent is one which is miscible with water, including but not limited to, alcohols and/or ketones. Preferable alcohols for this purpose include isopropanol, ethanol or methanol, but more preferably isopropanol. The precipitated carrageenan may then be separated from the solvent mixture. After separation, the carrageenan composition may be dried.

For some end-use applications of the carrageenan compositions of the present invention, it is especially desirable that the level of polyvalent cations be reduced to less than trace amounts. For reasons such as this, among others, it is sometimes desirable to expose the carrageenan composition to an ion-exchange process. This process can be performed in a variety of manners, but preferably includes exposing the carrageenan composition to an ion-exchange resin.

Additionally, other compounds may be added during the aforementioned process, as desired. For example, an antifoaming agent such as silicone oil is sometimes desirable during the extraction of the carrageenan composition from the carrageenan-containing starting material. Additionally, another gelling agent such as, for example, kappa carrageenan, may be added to the processed mixture prior to drying, if desired. The variations are numerous, and the present invention is not limited thereby.

Variations in the above-described process are sometimes desirable. For example, for some end-use applications it is unnecessary to separate the carrageenan compositions, as produced in accordance with the present invention, from the insoluble seaweed fraction. This can be accomplished in a number of marners. In one variation, the above described process may be performed, but without separating the carrageenan composition from the insoluble seaweed fraction. Briefly, extraction is performed as described above, i.e., extraction is preformed by heating the starting material in a solution at a mildly alkaline pH, and at a temperature sufficient to extract the carrageenan composition. Following extraction, the resulting mixture may be neutralized in a manner as described above. Preferably, the pH of the mixture following neutralization is from about 7 to about 9.5.

After neutralization, the mixture of extracted carrageenan and seaweed residue may be isolated by drying or by precipitation from the solvent. Precipitation may be performed as described above. The precipitated carrageenan and seaweed mixture may then be separated from the solvent mixture. After separation, the carrageenan and seaweed mixture may be dried.

In another variation, the seaweed (carrageenan-containing starting material) is exposed to conditions which are sufficient to modify the carrageenan within, i.e., convert iota carrageenan to nu carrageenan in the proper ratio, yet not result in removal of the carrageenan from the seaweed. For such a process, it is preferable to maintain the temperature during the modification below the temperature at which carrageenan is removed from the insoluble seaweed fraction. Typically, temperatures for this variation are from about 65° C. to about 90° C., more preferably from about 65° C. to about 80° C., and most preferably from about 65° C. to about 75° C. The alkali solution is then separated from the seaweed. The pH of the alkali-treated seaweed may be adjusted with an appropriate acid or through washing with water. The seaweed may then be washed and dried. The separated alkali solution can be recycled to be used in subsequent alkali treatments of seaweed. This process has industrial importance because it is simple, efficient, cost effective, reduces waste and results in reduced impact on the environment.

Carrageenan compositions of the present invention may be used in a variety of products, including foodstuffs for humans and animals, pharmaceutical products, veterinary products, cosmetics, personal care products and household products.

Foodstuffs produced in accordance with the present invention may be a water dessert comprising as a gelling agent a water-soluble carrageenan composition according to the present invention, preferably in an amount of about 0.4 to about 2.5% by weight of the final product, more particularly in an amount of about 0.6 to 1.3% by weight. Thus, an amount of water-soluble product according to the invention of 0.4 to 2.5% by weight in a water dessert is a cost-effective replacement of gelatin, yet providing the desirable properties of a gelatin-based water dessert in terms of temperature sensitivity, gununiness and ring at and below room temperatures and a watery mouth feel.

The present invention also relates to the use of the product as defined above in a milk desserts or processed meat products. Furthermore, the present invention relates to the use of the product in personal care products such as an oral care product, e.g., in toothpaste or skin care products. In addition, the present invention relates to the use of the products of the present invention in pharmaceutical applications, e.g., in topicals, lotions, and liquid gels suspensions and in household applications, e.g., air freshener gels, cleaning gels and the like.

EXAMPLES

The invention generally described above is now further described with the following Examples. These Examples are meant to be illustrative of some embodiments of the invention, but are not meant to limit the invention in any way. Other embodiments, both as apparent to those in the art and as described above, are included in this invention, which is limited only by the claims. Unless otherwise noted, parts and percentages, etc., are by weight.

TEST METHODS

In the following Examples, carrageenan compositions are prepared in accordance with the present invention. These carrageenan compositions are compared with comparative carrageenan compositions. A variety of tests are performed on the inventive and comparative carrageenan compositions. Additionally, carrageenan compositions of the present invention, comparative carrageenan compositions, and gelatin are compared in dessert gels. A variety of tests are performed on these dessert gels as well. Details of the test methods for testing the carrageenan compositions and the dessert gels are presented below.

$^{13}$C-NMR OF CARRAGEENAN COMPOSITIONS

A 250 mg sample of the carrageenan composition was dissolved in 10 ml $d_2$-$H_2O$ (deuterated) and mixed for 8 hours on a rotating mixer. The sample pH was then measured and adjusted if necessary to a final pH of 8. Ultrasonic degradation was performed for a total of 16 minutes at a temperature not exceeding 35° C.

The sample was then lyophilized and redissolved in $d_2$-$H_2O$ to make a 5wt % solution. $^{13}$C-NMR spectra are then acquired on either an AMX-400 or AMX-500 FT NMR spectrometer using the following conditions:sweep width— 235 ppm; probe temperature—80° C.; relaxation delay—5 seconds; acquisition mode—one pulse with nOe (nuclear Overhauser enhancement); number of scans—12,000–16, 000.

CHEMICAL ANALYSIS OF CARRAGEENAN COMPOSITION

The chemical analysis is based on the principle that galactose and 3,6-anhydro-galactose residues are converted to galactitol and 3,6-anhydro-galactictol by acid treatment of carrageenan. This treatment includes two reductive hydrolysis steps.

First, a mild acid hydrolysis was carried out in the presence of 4-methyl-morpholine-borane complex (MMB) and trifluoro acetic acid (TFA). During this mild hydrolysis, glycosidic linkages were be cleaved by keeping the 3,6-anhydro bridge in tact, due to the presence of MMB. The galactose units in the carrageenan were subsequently converted to galactitol residues whereas the 3,6-anhydro-galactose units were converted to 3,6-anhydro-galactitol residues. To achieve a complete reductive hydrolysis, a second hydrolysis with TFA is performed. The sugar alditols were analyzed quantitatively by HPLC using a Dionex High Performance Anion Exchange Chromatograph equipped with Pulsed Amperometric Detection (PAD).

IR ANALYSIS OF CARRAGEENAN COMPOSITION

Approximately 5 mg of powdered carrageenan sample was dissolved into 12 ml distilled water. The solution was allowed to stand overnight to ensure complete dissolution. Several drops (9–15) of the solution was then placed onto a 45° ZnSe horizontal attenuated total reflectance (ATR) crystal.

The crystal is then placed under a heat lamp and the liquid was evaporated to dryness, forming a thin film of carrageenan on the top of the ATR crystal. The sample and crystal were then placed into a Nicolet MAGNA 550 FT-IR and analyzed using 100 scans at 4 $cm^{-1}$ resolution.

MOLECULAR WEIGHT DETERMINATION

Analysis of molecular weight distribution of carrageenan compositions was determined by size exclusion chromatography (SEC).

Molecular weight calibration for the SEC column was obtained using poly (ethylene oxide) (PEO) narrow molecular weight standards. Thus, the molecular weight averages obtained are relative to PEO and are not absolute.

Size exclusion chromatography was performed according to the following procedures. The column set consisted of four TosoHaas TSK-Gel columns in series (3 GMPWXL mixed bed columns (Part No. 08025) and 1 G3000PWXL low pore size column (Part No. 08021)) available from Supelco, Bellefont, Pa. The relative molecular weight calibration was calculated from the peak elution times of a standard set of narrow molecular weight distribution poly (ethylene oxide) standards available from American Polymer Standards Corporation, Mentor, Ohio.

The calibration set encompassed 22 standards ranging in peak molecular weight from 106 to 1,702,000. The peak molecular weight of a narrow molecular weight standard is equal to the square root of (Mw/Mn) (ASTM test method D3536-76). The calibration curve is defined by a third degree polynomial curve fit of a plot of log MW vs. Ve/Vr, where Ve is elution volume of the standard and Vr is the elution volume of the reference peak, tetrahydrofaran (THF).

The columns and detector cell (Hewlett-Packard Differential Refractometer) were maintained at 40° C. The solvent (mobile phase) used was 0.10M lithium acetate with 0.10M glacial acetic acid (Aldrich Chemical Company, Milwaukee, Wis.). The final pH of the mobile phase is 4.8. The mobile phase reservoir is purged with helium. The flow rate of the analysis is 1 milliliter per minute. Samples were dissolved in the mobile phase at 0.20% wt/vol and filtered through a 0.45 micron pore size PVDF membrane filter (Millipore Corporation, Bedford, Mass.) prior to injection (200 microliters) into the chromatograph.

The reported molecular weights are the PEO equivalent molecular weights as calculated from the calibration curve. Data acquisition and analysis is performed using the Millennium 2020 Chromatography Data System GPC Package (Waters Corporation, Milford, Mass.).

RHEOLOGICAL CHARACTERISTICS

Rheological characteristics of carrageenan-containing preparations were performed using a Bohlin Vor Rheometer available from Bohlin Rheologi AB, SE. The measuring system was C-25; amplitude 90% on control box; torsion bar:10 to 20 g cm.

The following measurements were performed:1) temperature sweep (gelation) from 85° C. to 5° C.; frequency:1 Hz; 2) setting rate at 5° C.—end temperature 5° C. or 25° C.; frequency:1 Hz; 3) frequency sweep at 5° C. or 25° C.; frequency:0.01–20 Hz; 4) strain sweep at 5° C. or 25° C.; frequency 1 Hz; and 5) temperature sweep (melting) from 5° C. or 25° C. to 85° C.; frequency:1 Hz.

Elastic modulus (G'—1 Hz, 5° C.) is determined as follows:from frequency sweep at 5° C. a reading of the strain is taken at 1 Hz. The strain sweep is then taken at 5° C. and a reading of the elastic modulus, G', is made at this strain.

Elastic modulus (G'—1 Hz, 25° C.) is determined as follows:from frequency sweep at 25° C. a reading of the strain is taken at 1 Hz. The strain sweep is then taken at 5° C. and a reading of the elastic modulus, G', is made at this strain.

Viscous modulus (G"—0.2 Hz, 5° C.) is determined as follows: from frequency sweep at 5° C. a reading of the viscous modulus, G", is made at 0.2 Hz.

Melting point is measured at G'=1 from temperature sweep curve.

TEXTURAL CHARACTERISTICS

For the textural analysis, the gelling agent was present at 1.2 wt %. The gels were tested on a TA-XT2 Texture Analyzer, manufactured by Stable Micro Systems. This device was used for measurement of break strength, gel strength, break distance, and negative area. Break strength (BS) is the force (in grams) required to compress the gel to the point of break with a one inch diameter probe. Gel strength (GS) is the force (in grams) required to compress the gel to a predetermined depth of 2 mm, 8 mm, and 15 mm with a one inch diameter probe. Break distance (BD) is the distance (in mm) the probe travels to break a gel. In these experiments the probe speed is 1 mm/sec. Negative area (NA) is the area (g·sec) below the x-axis when a plot of force as a function of compression time is plotted as the probe is withdrawn from the sample.

Example 1

SODIUM CARBONATE EXTRACTION OF IOTA CARRAGEENAN FROM *EUCHEUMA SPINOSUM*

1000 grams of dried *Eucheuma spinosum* seaweed (70% dry matter) was weighed out and was added to a mixture of 90 grams of sodium carbonate and 7 liters of water (corresponding to 0.12 mol $Na_2CO_3$ per liter) in an autoclave. The mixture was then heated while stirring at 115° C. for three hours.

The pressure was reduced in the autoclave and the mixture was cooled to about 95° C., after which the mixture was diluted with three volumes of water to facilitate filtration. The mixture was allowed to stand at 95° C. for an additional three hours, and then the mixture was neutralized with carbon dioxide to a pH of about 9–9.5.

The carrageenan extract was separated from the seaweed residue by filtration on Celite™ 545 filter aid manufactured by Celite, Iceland. The carrageenan was precipitated with three volumes of 80% isopropyl alcohol, and the precipitate was dried in a heating chamber overnight.

The yield was 12.7 grams per liter, corresponding to 49.9% of 100% seaweed dry matter.

Comparative Example 1

CALCIUM HYDROXIDE EXTRACTION OF CARRAGEENAN FROM *EUCHEUMA SPINOSUM*

Using the same procedure as in Example 1 above, replacing 90 grams of sodium carbonate per 7 liters of water with 50 grams of calcium hydroxide in 7 liters of water, the yield obtained was 10.9 grams per liter, corresponding to 42.2% of 100% seaweed dry matter. Thus, the use of sodium carbonate instead of the conventionally used calcium hydroxide surprisingly increases the yield by more than 18%.

Examples 2–63

ADDITIONAL EXAMPLES OF EXTRACTION OF CARRAGEENAN FROM *EUCHEUMA SPINOSUM*

Additional inventive and comparative examples are presented in TABLES I–V. The examples set forth in TABLES I–III are performed essentially as described in Example 1, with the exception of the differences which are set forth in the column labeled "Sample Treatment."

The following terms are used in TABLES I–III: Retention—period of time after the pressure is removed from the autoclave that the extraction material is held before further processing (period of time between extraction and neutralization, for example); concentrate—high seaweed to water ratio (1:7) compared to standard procedure (1:50); UF-conc.—ultrafiltration concentration of extract; grinding (– or +)—with or without mechanical disintegration of the wet extraction material; fully modified—complete conversion of Nu to Iota form (or mu to kappa for Chondrus and Gigartina); full calcium—complete conversion of Nu to Iota form using calcium hydroxide; low modified—incomplete conversion of the Nu to iota form (and mu to kappa); soda—sodium carbonate, $Na_2CO_3$; lime—calcium hydroxide, $Ca(OH)_2$; potash—potassium carbonate, $K_2CO_3$; neutral HCl—neutralization with hydrochloric acid; IE—calcium ions exchanged with sodium using $Na_2CO_3$; SUPER IE—ion exchange as with IE plus treatment with Amberlite ABH–252 ion exchange resin; "Desired Properties" is judged subjectively considering all of the properties together, and ++, +, and –, indicate highly desirable, desirable, and undesirable organoleptic properties, respectively.

TABLE I

| Example | Sample treatment | Desired Properties | K mg/g | Na mg/g | Ca mg/g | Mg mg/g | K % | Na % | Ca % | Mg % | Mw Daltons |
|---|---|---|---|---|---|---|---|---|---|---|---|
| 2 | 10% soda, 115° C. 3 h (concentrate), 2 h retention | ++ | 50.96 | 42.12 | 0.53 | | 5.46 | 3.83 | 0.06 | 0.19 | 682648.00 |
| 3 | 7% lime, 90° C. 45 min. Neutral HCl. | ++ | 28.00 | 9.00 | 56.00 | | | | | | |
| 4 | 9% soda#115° C. 35 min (concentrate) 18 h retention | ++ | | | | | 5.60 | 3.59 | 0.02 | 0.11 | 668470.00 |
| 5 | 10% soda, 98° C. 35 min, 3 h retention – grinding. | ++ | | | | | 3.73 | 6.02 | 0.08 | 0.18 | 813437.00 |
| 6 | 6.5% potassium carbonate,115° C. 3 h (concentrate), 18 h retention | ++ | 100.56 | 18.64 | 0.36 | | 9.42 | 1.82 | 0.06 | 0.11 | 642361.00 |
| 7 | 10% soda, 115° C. 35 min (concentrate), 18 h retention | ++ | 48.00 | 44.28 | 0.54 | | 5.15 | 3.90 | 0.07 | 0.23 | 704892.00 |
| 8 | 13% potassium carbonate, 115° C. 3 h (concentrate), 2 h retention | ++ | 105.76 | 14.20 | 0.50 | | 9.76 | 1.39 | 0.08 | 0.20 | 643854.00 |
| 9 | 20% soda, 115° C. 35 min, 3 h retention + grinding. | ++ | 43.31 | 48.83 | 0.75 | 2.73 | | | | | 836602.00 |
| 10 | 15% soda, 115° C. 35 min (concentrate) 3 h retention | ++ | 47.68 | 51.89 | 1.15 | | | | | | 763380.00 |
| 11 | 20% soda 110° C. 35 min, 3 h retention | ++ | 45.60 | 47.92 | 0.62 | 3.00 | | | | | 830923.00 |
| 12 | 7% lime 100° C. 45 min. Neutral HCl. | ++ | 28.00 | 9.00 | 56.00 | | | | | | |
| 13 | 26% potassium carbonate, 110° C. 35 min, 18 h retention – grinding. | ++ | 105.04 | 12.06 | 0.53 | | 10.30 | 1.15 | 0.09 | 0.23 | 669934.00 |
| 14 | 7% lime 90° C. 120 min. Neutral HCl. | ++ | 28.00 | 9.00 | 56.00 | | | | | | |
| 15 | 13.5% potash, 115° C. 3 h, 18 h retention | ++ | 106.00 | 19.24 | 0.36 | | | | | | |
| 16 | 15% soda, 115° C. 35 min (concentrate) 18 h retention | ++ | 47.12 | 52.00 | 0.46 | | | | | | 806227.00 |
| 17 | 10% soda, 115° C. 3 h (concentrate), 3–5 h retention. UF-conc. | + | 44.92 | 47.92 | 0.29 | 0.56 | | | | | 626961.00 |
| 18 | 10% soda, 115° C. 3 h (concentrate), 3–5 h retention. UF-conc. | + | 38.56 | 50.64 | 0.38 | 0.35 | | | | | 659799.00 |
| 19 | 10% soda, 115° C. 3 h (concentrate), 3–5 h retention. UF-conc. | + | 45.92 | 47.40 | 0.30 | 0.65 | | | | | 598326.00 |
| 20 | 5% soda, 115° C. 3 h (concentrate), 2 h retention | + | 60.92 | 36.99 | 1.17 | | | | | | 658450.00 |
| 21 | 20% soda, 110° C. 35 min, 1 h retention – grinding. | + | | | | | 4.04 | 4.76 | 0.08 | 0.02 | 688665.00 |
| 22 | 8,8% lime, 70° C. 35 min, 3 h retention – grinding. | + | 59.42 | 22.26 | 37.26 | 3.61 | | | | | 609302.00 |
| 23 | 20% soda, 110° C. 35 min, 3 h retention – grinding. | + | | | | | 4.05 | 4.76 | 0.04 | 0.01 | 905864.00 |
| 24 | 8.8% lime, 110° C. 35 min, 18 h retention + grinding. | – | 52.03 | 18.70 | 29.50 | 3.59 | | | | | 600120.00 |
| 25 | 5% soda, 115° C. 35 min (concentrate), 2 h retention | – | 62.00 | 39.88 | 0.73 | | | | | | 724932.00 |
| 26 | ATC-extract | – | | | | | 4.99 | 1.01 | 0.11 | 0.29 | 462939.00 |
| 27 | Fully modified calcium Chondrus | – | | | | | 2.34 | 1.68 | 3.46 | 0.01 | 713255.00 |
| 28 | 26% potasiumcarbonat, 110° C. 35 min, 2 h retention – grinding | – | 103.76 | 11.57 | 0.64 | | 10.40 | 1.10 | 0.11 | 0.22 | 729494.00 |
| 29 | Fully modified calcium Giganina | – | | | | | 2.06 | 2.65 | 4.01 | 0.03 | 628596.00 |
| 30 | Full calcium, 110° C. 35 min, no retention, neutralize, IE | – | 56.00 | 39.80 | 0.70 | | 5.90 | 3.63 | 0.07 | 0.02 | 504284.00 |
| 31 | 20% soda 70° C. 35 min, 3 h retention | – | 43.96 | 53.48 | 1.77 | 4.72 | | | | | 1010768.00 |
| 32 | Fully modified calcium Spinosum ion-exchanged to Na. | – | | | | | 2.08 | 6.43 | 0.03 | 0.01 | 652982.00 |
| 33 | 8.8% lime, 110° C. 35 min, 3 h retention – grinding. | – | 44.63 | 13.19 | 42.12 | 3.16 | | | | | 630920.00 |
| 34 | 8.8% lime, 110° C. 35 min, 3 h retention + grinding. | – | 44.13 | 17.25 | 36.95 | 6.66 | | | | | 797786.00 |
| 35 | 8.8% lime, 110° C. 35 min, 3 h retention + ionext. soda | – | 37.96 | 54.96 | 11.34 | 1.12 | | | | | 774010.00 |
| 36 | 0% soda 110° C. 35 min, 3 h retention | – | 60.72 | 23.00 | 6.91 | 8.30 | | | | | 862922.00 |
| 37 | 10.7% NH4CO3, 115° C. 3 h, 18 h retention. | – | 68.60 | 27.32 | 0.72 | | | | | | |
| 38 | 8.8% lime, 115° C. 35 min, 3 h retention + grinding. | – | 47.64 | 17.32 | 38.82 | 5.37 | | | | | 680218.00 |
| 39 | Low modified calcium Gigantina | — | | | | | 1.50 | 4.02 | 1.31 | 0.33 | 645878.00 |
| 40 | 8.8% lime, 110° C. 35 min, 18 h retention + grinding. | – | 58.44 | 19.83 | 34.24 | 1.90 | | | | | 706518.00 |
| 41 | 5,4% NH4CO3, 115° C. 3 h, 2 h retention. | – | 70.12 | 25.60 | 1.49 | | | | | | |
| 42 | Fully modified calcium Spinosum | – | | | | | 5.25 | 1.90 | 3.19 | 0.02 | 717524.00 |
| 43 | Full calcium, 110° C. 35 min, no retention, neutralize, IE | – | 57.20 | 42.20 | 0.25 | | | | | | 576822.00 |
| 44 | 8.8% lime, 110° C. 35 min, 3 h retention + grinding. | – | 55.46 | 17.61 | 45.57 | 5.87 | | | | | 749342.00 |
| 45 | Full calcium, 110° C. 35 min, no | – | 56.70 | 39.60 | 0.35 | | | | | | 520846.00 |

TABLE I-continued

| Example | Sample treatment | Desired Properties | K mg/g | Na mg/g | Ca mg/g | Mg mg/g | K % | Na % | Ca % | Mg % | Mw Daltons |
|---|---|---|---|---|---|---|---|---|---|---|---|
| | retention, neutralize, IE | | | | | | | | | | |
| 46 | 9% soda, 115° C. 35 min (concentrate), 2 h retention | – | | | | | 5.69 | 3.85 | 0.04 | 0.11 | 490304.00 |
| 47 | 8.8% lime, 110° C. 35 min, 18 h retention + grinding. | – | 59.45 | 19.24 | 37.61 | 1.68 | | | | | 756130.00 |
| 48 | 5% soda, 115° C. 35 min (concentrate), 18 h retention | – | 61.52 | 37.96 | 0.64 | | 6.41 | 3.18 | 0.08 | 0.19 | 772906.00 |
| 49 | 8.8% lime, 110° C. 35 min, 18 h retention + grinding. | – | 51.11 | 18.15 | 34.62 | 4.73 | | | | | 539613.00 |
| 50 | 20% soda, 110° C. 35 min, 3 h retention – grinding. | – | 40.04 | 55.50 | 0.86 | | | | | | 770320.00 |
| 51 | 8.8% lime, 70° C. 35 min, 18 h retention + grinding. | – | 52.56 | 19.87 | 32.72 | 2.34 | | | | | 432346.00 |
| 52 | 7% lime, 100° C. 120 min. Neutral HCl. | – | 28.00 | 9.00 | 56.00 | | | | | | |
| 53 | Neutral Cottonii | – | | | | | 6.18 | 1.44 | 0.26 | 0.19 | 244012.00 |
| 54 | Neutra Spinosum | – | | | | | 6.77 | 1.82 | 0.89 | 0.23 | 513473.00 |
| 55 | 6.5% potasiumcarbonat, 115° C. 3 h (concentrate), 2 h retention | – | 96.88 | 18.64 | 0.41 | | 9.53 | 1.82 | 0.08 | 0.11 | 714860.00 |
| 56 | Fully modified calcium Spinosum ion-exchanged to K. | — | | | | | 12.00 | 0.93 | 0.02 | 0.01 | 626246.00 |
| 57 | 8.8% lime, 115° C. 35 min, 18 h retention – grinding. | – | 55.80 | 21.42 | 24.76 | 2.87 | | | | | 625218.00 |
| 58 | 1% soda 110° C. 35 min, 3 h retention | – | 66.80 | 24.08 | 4.78 | 4.50 | | | | | 981139.00 |

TABLE II

| Example | Sample treatment | Poly-disp Index | Sulphate % | NMR (mole %) | | | | | IR | |
|---|---|---|---|---|---|---|---|---|---|---|
| | | | | Iota G4S-DA2S | Nu G4S-D(2),6S | Kappa G4S-DA | Starch | Other | Peak | Mole % Nu |
| 2 | 10% soda, 115° C. 3 h (concentrate), 2 h retention | 4.62 | 33.72 | 88.70 | 5.20 | | 1.70 | 4.40 | 963.80 | 3.20 |
| 3 | 7% lime, 90° C. 45 min. Neutral HCl. | | | 87.50 | 8.80 | | 3.70 | | | |
| 4 | 9% soda, 115° C. 35 min (concentrate), 18 h retention | 3.89 | 34.73 | | | | | | 965.10 | 5.60 |
| 5 | 10% soda, 98° C. 35 min, 3 h retention – grinding. | 4.00 | 34.40 | | | | | | 966.20 | 7.60 |
| 6 | 6.5% potassium carbonate, 115° C. 3 h (concentrate), 18 h retention | 4.14 | 33.37 | | | | | | 966.50 | 8.10 |
| 7 | 10% soda, 115° C. 35 min (concentrate), 18 h retention | 4.23 | 34.04 | 88.40 | 6.60 | | 1.80 | 3.20 | 964.20 | 4.00 |
| 8 | 13% potassium carbonate, 115° C. 3 h (concentrate), 2 h retention | 3.88 | 33.55 | 86.50 | 5.80 | | 4.60 | 3.10 | 965.20 | 5.80 |
| 9 | 20% soda, 115° C. 35 min, 3 h retention + grinding. | 4.45 | 34.40 | | | | | | 967.00 | 9.00 |
| 10 | 15% soda, 115° C. 35 min (concentrate), 3 h retention | 4.75 | 33.77 | | | | | | 965.00 | 5.40 |
| 11 | 20% soda 110° C. 35 min, 3 h retention | | 34.40 | | | | | | | |
| 12 | 7% lime, 100° C. 45 min. Neutral HCl. | | | 92.40 | 4.70 | | 2.80 | | | |
| 13 | 26% potassium carbonate, 110° C. 35 min, 18 h retention – grinding. | 4.12 | 34.12 | | | | | | 964.30 | 4.10 |
| 14 | 7% lime, 90° C. 120 min. Neutral HCl. | | | 95.50 | 2.10 | | 2.40 | | | |
| 15 | 13.5% potash, 115° C. 3 h, 18 h retention | | | 85.80 | 3.10 | | 5.30 | 5.80 | | |
| 16 | 15% soda, 115° C. 35 min (concentrate), 18 h retention | 4.54 | 33.92 | | | | | | 963.30 | 2.30 |
| 17 | 10% soda, 115° C. 3 h (concentrate), 3–5 h retention. UF-conc. | 4.36 | 32.88 | 96.70 | | | | 3.30 | 962.40 | 0.70 |
| 18 | 10% soda, 115° C. 3 h (concentrate), 3–5 h retention. UF-conc. | 4.05 | 34.83 | 95.10 | | | | 4.90 | 962.40 | 0.70 |
| 19 | 10% soda, 115° C. 3 h (concentrate), 3–5 h retention. UF-conc. | 3.95 | 33.91 | 95.90 | | | | 4.10 | 962.30 | 0.50 |
| 20 | 5% soda, 115° C. 3 h (concentrate), 2 h retention | 4.31 | 33.95 | | | | | | 966.60 | 8.30 |
| 21 | 20% soda, 110° C. 35 min, 1 h retention grinding. | 3.87 | 34.83 | 85.10 | 6.70 | | | 8.20 | 965.90 | 7.00 |
| 22 | 8.8% lime, 70° C. 35 min , 3 h retention – grinding. | 4.59 | 34.97 | | | | | | 965.20 | 5.80 |
| 23 | 20% soda, 110° C. 35 min, 3 h retention – grinding. | 4.31 | 34.35 | 86.30 | 7.10 | | | 6.60 | 965.20 | 5.80 |
| 24 | 8.8% lime, 110° C. 35 min, 18 h retention + grinding. | 4.11 | 33.93 | | | | | | 962.30 | 0.50 |
| 25 | 5% soda, 115° C. 35 min (concentrate). 2 h | 4.42 | 33.87 | | | | | | 967.40 | 9.70 |

TABLE II-continued

| Example | Sample treatment | Poly-disp Index | Sulphate % | NMR (mole %) Iota G4S-DA2S | Nu G4S-D(2),6S | Kappa G4S-DA | Starch | Other | IR Peak | Mole % Nu |
|---|---|---|---|---|---|---|---|---|---|---|
| | retention | | | | | | | | | |
| 26 | ATC-extract | 4.62 | 22.46 | | | | | | 970.00 | 14.40 |
| 27 | Fully modified calcium Chondrus | 5.17 | 26.62 | | | | | | 970.60 | 15.50 |
| 28 | 26% potassium carbonate, 110° C. 35 min, 2 h retention – grinding. | 5.39 | 33.22 | 80.00 | 11.00 | | | 9.00 | 968.10 | 11.00 |
| 29 | Fully modified calcium Gigantina | 4.49 | 30.66 | 32.60 | | 52.20 | | | 967.70 | 10.30 |
| 30 | Full calcium, 110° C. 35 min, no retention, neutralize, IE | 4.60 | 33.84 | 89.90 | | | 5.60 | 4.60 | 962.50 | 0.90 |
| 31 | 20% soda 70° C. 35 min, 3 h retention | | 34.70 | | | | | | | |
| 32 | Fully modified calcium Spinosum ion-exchanged to Na. | 4.65 | 34.39 | 96.80 | | 3.20 | | | 962.30 | 0.50 |
| 33 | 8.,8% lime, 110° C. 35 min, 3 h retention – grinding. | 4.51 | 34.54 | | | | | | 962.10 | 0.20 |
| 34 | 8.8% lime, 110° C. 35 min, 3 h retention + grinding. | 4.82 | 34.61 | | | | | | 962.40 | 0.70 |
| 35 | 8.8% lime, 110° C. 35 min, 3 h retention + ionext. soda | | 34.10 | | | | | | | |
| 36 | 0% soda 110° C. 35 min, 3 h retention | | 31.70 | | | | | | | |
| 37 | 10.7% NH4CO3, 115° C. 3 h, 18 h retention. | | | 77.90 | 11.30 | | 5.00 | 5.90 | | |
| 38 | 8.8% lime, 115° C. 35 min, 3 h retention + grinding. | 4.56 | 34.19 | | | | | | 962.10 | 0.20 |
| 39 | Low modified calcium Gigantina | 6.08 | 33.04 | 23.90 | 21.90 | 54.30 | | | ? | ? |
| 40 | 8.8% lime, 110° C. 35 min, 18 h retention + grinding. | 4.10 | 34.23 | | | | | | 961.90 | (0.20) |
| 41 | 5.4% NH4CO3, 115° C. 3 h, 2 h retention. | | | 82.00 | 11.70 | | 3.10 | 3.10 | | |
| 42 | Fully modified calcium Spinosum | 5.04 | 34.05 | | | | | | 962.30 | 0.50 |
| 43 | Full calcium, 110° C. 35 min, no retention, neutralize, IE | 4.07 | 34.10 | 92.20 | | | 3.20 | 4.60 | 962.10 | 0.20 |
| 44 | 8.8% lime, 110° C. 35 min, 3 h retention + grinding. | 4.92 | 33.94 | | | | | | 962.20 | 0.40 |
| 45 | Full calcium, 110° C. 35 min, no retention, neutralize, E | 4.12 | 33.60 | | | | | | 962.20 | 0.40 |
| 46 | 9% soda, 115° C. 35 min (concentrate), 2 h retention | 3.61 | 34.03 | 81.30 | 10.30 | | 2.40 | 6.10 | 966.20 | 7.60 |
| 47 | 8.8% lime, 110° C. 35 min, 18 h retention + grinding. | 4.16 | 34.20 | | | | | | 964.00 | 3.60 |
| 48 | 5% soda, 115° C. 35 min (concentrate), 18 h retention | 5.40 | 34.29 | 84.00 | 10.10 | | 2.10 | 3.80 | 966.90 | 8.80 |
| 49 | 8.8% lime, 110° C. 35 min, 18 h retention + grinding. | 3.83 | 33.66 | | | | | | 963.50 | 2.70 |
| 50 | 20% soda, 110° C. 35 min 3 h retention – grinding. | 4.17 | 33.46 | | | | | | 966.30 | 7.80 |
| 51 | 8.8% lime, 70° C. 35 min, 18 h retention + grinding. | 4.08 | 34.55 | | | | | | 964.30 | 4.10 |
| 52 | 7% lime, 100° C. 120 min. Neutral HCl. | | | 96.90 | | | 3.10 | | | |
| 53 | Neutral Cottonii | 3.43 | 24.86 | | | | | | 972.00 | 18.00 |
| 54 | Neutral Spinosum | 5.34 | 33.12 | | | | | | 967.30 | 9.60 |
| 55 | 6.5% potassium carbonate, 115° C. 3 h (concentrate), 2 h retention | 4.36 | 34.11 | 87.10 | 9.40 | | | 3.50 | 967.20 | 9.40 |
| 56 | Fully modified calcium Spinosum ion-exchanged to K. | 4.57 | 35.01 | | | | | | 962.30 | 0.50 |
| 57 | 8.8% lime, 115° C. 35 min, 18 h retention – grinding. | 4.08 | 34.54 | | | | | | 963.30 | 2.30 |
| 58 | 1% soda 110° C. 35 min, 3 h retention | | 33.50 | | | | | | | |

TABLE III

| Example | Sample treatment | Chemical 3,6AG (% AM) | Texture Analysis 8 mm Force (g) | 15 mm Force (g) | Break Strength | Distance Traveled | Neg Area | pH before ext | pH after ext |
|---|---|---|---|---|---|---|---|---|---|
| 2 | 10% soda, 115° C. 3 h (concentrate), 2 h retention | 88.00 | 62.82 | 145.12 | 399.37 | 27.47 | −2478.63 | | |
| 3 | 7% lime, 90° C. 45 min. Neutral HCl. | | | | | | | | |
| 4 | 9% soda, 115° C. 35 min (concentrate), 18 h retention | | 74.44 | 167.67 | 521.06 | 29.95 | −3288.43 | | |
| 5 | 10% soda, 98° C. 35 min, 3 h retention – grinding. | | 47.96 | 101.65 | 403.40 | 31.77 | −1476.00 | | |

TABLE III-continued

| | | Chemical | Texture Analysis | | | | | pH | |
|---|---|---|---|---|---|---|---|---|---|
| | | | 8 mm | | | | | | |
| Example | Sample treatment | 3,6AG (% AM) | Force (g) | 15 mm Force (g) | Break Strength | Distance Traveled | Neg Area | before ext | after ext |
| 6 | 6.5% potassium carbonate, 115° C. 3 h (concentrate), 18 h retention | | 55.60 | 125.07 | 400.42 | 30.67 | −2016.36 | | |
| 7 | 10% soda, 115° C. 35 min (concentrate), 18 h retention | 88.00 | 70.90 | 156.55 | 503.19 | 29.43 | −3702.39 | | |
| 8 | 13% potassium carbonate, 115° C. 3 h (concentrate), 2 h retention | | 71.98 | 162.45 | 332.01 | 26.48 | −3323.80 | | |
| 9 | 20% soda, 115° C. 35 min, 3 h retention + grinding. | 80.00 | 34.22 | 75.07 | 261.02 | 30.26 | −912.97 | 9.79 | 9.42 |
| 10 | 15% soda, 115° C. 35 min (concentrate), 3 h retention | 82.00 | 54.79 | 123.35 | 485.69 | 31.71 | −1760.84 | | |
| 11 | 20% soda 110° C. 35 min, 3 h retention | 82.00 | | | | | | | |
| 12 | 7% lime, 100° C. 45 min. Neutral HCl. | | | | | | | | |
| 13 | 26% potassium carbonate, 110° C. 35 min, 18 h retention − grinding. | | 60.55 | 131.29 | 286.39 | 26.54 | −2515.30 | | |
| 14 | 7% lime, 90° C. 120 min. Neutral HCl. | | | | | | | | |
| 15 | 13.5% potash, 115° C. 3 h, 18 h retention | | | | | | | | |
| 16 | 15% soda, 115° C. 35 min (concentrate), 18 h retention | 92.00 | 60.01 | 134.80 | 407.31 | 29.45 | −2590.33 | | |
| 17 | 10% soda, 115° C. 3 h (concentrate), 3–5 h retention. UF-conc. | 90.00 | 55.96 | 121.76 | 289.74 | 25.75 | −2591.11 | | |
| 18 | 10% soda, 115° C. 3 h (concentrate), 3–5 h retention. UF-conc. | 90.00 | 56.62 | 126.37 | 267.12 | 25.06 | −2367.09 | | |
| 19 | 10% soda, 115° C. 3 h (concentrate), 3–5 h retention. UF-conc. | 92.00 | 52.69 | 116.36 | 240.83 | 24.15 | −2377.64 | | |
| 20 | 5% soda, 115° C. 3 h (concentrate), 2 h retention | 80.00 | 39.68 | 92.34 | 309.15 | 30.07 | −1041.70 | | |
| 21 | 20% soda, 11000 35 min, 1 h retention − grinding. | | 42.59 | 95.00 | 285.29 | 28.67 | −1234.74 | | |
| 22 | 8.8% lime, 70° C. 35 min , 3 h retention − grinding. | 86.00 | 41.00 | 93.47 | 370.58 | 31.25 | −1098.40 | 10.65 | 10.72 |
| 23 | 20% soda, 110° C. 35 min, 3 h retention − grinding. | | 52.92 | 110.84 | 791.99 | 33.99 | −765.40 | | |
| 24 | 8.8% lime, 110° C. 35 min, 18 h retention + grinding. | 102.00 | 41.24 | 97.30 | 217.89 | 24.75 | −1792.57 | 10.45 | 10.05 |
| 25 | 5% soda, 115° C. 35 min (concentrate), 2 h retention | 80.00 | 23.20 | 52.57 | 197.98 | 30.97 | −453.47 | | |
| 26 | ATC-extract | | | | 1990.49 | 4.44 | −4888.45 | | |
| 27 | Fully modified calcium Chondrus | | | | | | | | |
| 28 | 26% potassium carbonate, 110° C. 35 min, 2 h retention − grinding. | | 29.04 | 65.59 | 207.76 | 29.47 | −527.62 | | |
| 29 | Fully modified calcium Gigantina | | | | | | | | |
| 30 | Full calcium, 110° C. 35 min, no retention, neutralize, IE | 98.00 | 36.75 | 82.81 | 152.17 | 22.13 | −1271.75 | | |
| 31 | 20% soda 70° C. 35 min, 3 h retention | 80.00 | | | | | | | |
| 32 | Fully modified calcium Spinosum ion-exchanged to Na. | | 50.40 | 114.53 | 290.38 | 25.05 | −1962.90 | | |
| 33 | 8.8% lime, 110° C. 35 min, 3 h retention − grinding. | 98.00 | 49.73 | 116.65 | 268.52 | 25.33 | −2546.64 | 10.60 | 10.22 |
| 34 | 8.8% lime, 110° C. 35 min, 3 h retention + grinding. | 94.00 | 43.84 | 100.49 | 316.15 | 27.72 | −2493.44 | 10.56 | 10.10 |
| 35 | 8.8% lime, 110° C. 35 min, 3 h retention + ion ext. soda | 98.00 | | | | | | | |
| 36 | 0% soda 110° C. 35 min, 3 h retention | 75.00 | | | | | | | |
| 37 | 10.7% NH4CO3, 115° C. 3 h, 18 h retention. | | | | | | | | |
| 38 | 8.8% lime, 115° C. 35 min, 3 h retention + grinding. | 96.00 | 53.33 | 123.86 | 349.52 | 27.25 | −3193.31 | 10.60 | 10.11 |
| 39 | Low modified calcium Giganina | | | | | | | | |
| 40 | 8.8% lime, 110° C. 35 min, 18 h retention + grinding. | 98.00 | 47.95 | 112.75 | 379.07 | 27.76 | −2187.26 | 10.34 | 9.95 |
| 41 | 5.4% NH4CO3, 115° C. 3 h, 2 h retention. | | | | | | | | |
| 42 | Fully modified calcium Spinosum | | 29.00 | 66.78 | 147.77 | 24.52 | −1106.19 | | |
| 43 | Full calcium, 110° C. 35 min, no retention, neutralize, IE | 98.00 | 34.41 | 77.68 | 150.32 | 22.64 | −1157.18 | | |
| 44 | 8.8% lime, 110° C. 35 min, 3 h retention + grinding. | 96.00 | 45.22 | 103.88 | 397.88 | 28.83 | −2136.56 | 10.50 | 10.03 |
| 45 | Full calcium, 11D° C. 35 min, no | 96.00 | 32.30 | 71.17 | 141.98 | 23.05 | −1046.29 | | |

TABLE III-continued

| | | | Texture Analysis | | | | | pH | |
|---|---|---|---|---|---|---|---|---|---|
| | | Chemical | 8 mm | | | | | | |
| Example | Sample treatment | 3,6AG (% AM) | Force (g) | 15 mm Force (g) | Break Strength | Distance Traveled | Neg Area | before ext | after ext |
| | retention, neutralize, IE | | | | | | | | |
| 46 | 9% soda, 115° C. 35 min (concentrate), 2 h retention | | 36.91 | 84.26 | 190.64 | 26.48 | −931.34 | | |
| 47 | 8.8% lime, 110° C. 35 min, 18 h retention + grinding. | 102.00 | 49.49 | 114.15 | 377.27 | 27.68 | −2276.50 | 10.47 | 10.10 |
| 48 | 5% soda, 115° C. 35 min (concentrate), 18 h retention | 80.00 | 42.53 | 94.21 | 375.58 | 31.79 | −1168.95 | | |
| 49 | 8.8% lime, 110° C. 35 min, 18 h retention + grinding. | 96.00 | 38.25 | 87.16 | 194.36 | 24.08 | −1687.69 | 10.55 | 10.10 |
| 50 | 20% soda, 110° C. 35 min, 3 h retention − grinding. | 80.00 | 40.12 | 91.14 | 425.27 | 31.72 | −952.67 | | |
| 51 | 8.8% lime, 70° C. 35 min, 18 h retention + grinding. | 98.00 | 57.67 | 127.01 | 244.68 | 22.39 | −2748.06 | 11.10 | 10.61 |
| 52 | 7% lime, 100° C. 120 min. Neutral HCl. | | | | | | | | |
| 53 | Neutral Cottonii | | | | | | | | |
| 54 | Neutral Spinosum | | | | | | | | |
| 55 | 6.5% potassium carbonate, 115° C. 3 h (concentrate), 2 h retention | | 38.33 | 87.10 | 277.03 | 29.90 | −1045.72 | | |
| 56 | Fully modified calcium Spinosum ion-exchanged to K. | | 47.22 | 112.49 | 275.48 | 25.07 | −1799.16 | | |
| 57 | 8.8% lime, 115° C. 35 min , 18 h retention − grinding. | 96.00 | 46.68 | 103.64 | 211.38 | 23.77 | −1527.95 | 10.27 | 10.00 |
| 58 | 1% soda 110° C. 35 min, 3 h retention | 75.00 | | | | | | | |

Example 64

USE OF CARRAGEENAN COMPOSITION IN MODEL WATER DESSERT GELS

The carrageenans produced in Example 1 and Comparative Example 1 have been evaluated in a model water dessert as described below.

| Ingredients | Parts |
|---|---|
| Fine mesh (30 mesh) sugar (sucrose) | 15.00 |
| Tri-potassium citrate, monohydrate | 0.30 |
| Calcium chloride, dihydrate | 0.15 |
| Citric acid, anhydrous | 0.20 |
| Gelling agent | X |
| Demineralized water | 84.35 − X |
| Total | 100.00 |

Carrageenan: X = 1.0 or 1.20
Gelatin: X = 1.2 or 2.00

The dry ingredients were weighed and mixed well and boiling water was added while stirring vigorously to form a solution. At this point the solution was divided into two portions for rheological and textural analysis.

Figure 2:
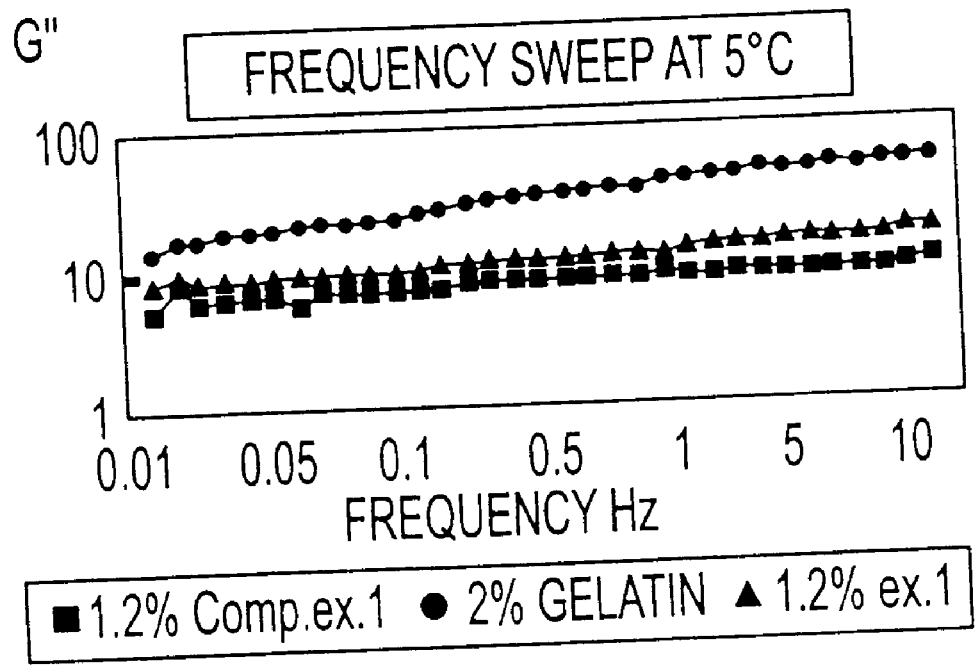
FIG. 2 shows frequency sweep of a carrageenan according to the invention as well as of a comparative carrageenan and of gelatin.

The rheological characteristics of the dessert preparation was determined at 5° C. and 25° C. by means of a rheometer Bohlin VOR, available from Bohlin Rheologi AB, SE using a Bohlin measuring cup C-25. The first portion was transferred hot (min. 80° C.) to the cup and gelled in a controlled manner. During gelation a temperature sweep (gelation), a setting rate determination, frequency sweep (FIG. 2), strain sweep (FIGS. 1A–1F) and temperature sweep (melting) were measured. In the strain sweep curves (FIGS. 1A–1F), G'/in is read from the linear portion of the G' vs. Strain curve, and G'/in is the value, in Pa, at the linear portion of the curve. Measurements were preformed as described above under Test Methods. TABLE IV below shows rheological values obtained.

TABLE IV

| | Rheological Characteristics of Dessert Preparations | | | | | | |
|---|---|---|---|---|---|---|---|
| | Elastic | Gel strength loss | | Viscous Modulus G", Pa | G'/G" | Complex viscosity, µ | Phase Angle[3] |
| Gelling agent[1] | Modulus G', 5° C. | ΔG' Pa | % | 0.2 Hz 5° C. | 0.2 Hz 5° C. | Pa, 25° C. 5 Hz | δ, 5° C. 5 Hz |
| 1.2% ex. 1[2] | 247 | 79 | 32 | 10.9 | 23 | 5.6 | 3.4 |
| 1.2% comp. ex. 1 | 188 | (−4) | (−2) | 7.4 | 25 | 0.1 | 2.6 |

TABLE IV-continued

Rheological Characteristics of Dessert Preparations

| Gelling agent[1] | Elastic Modulus G', 5° C. | Gel strength loss ΔG' Pa | Gel strength loss % | Viscous Modulus G", Pa 0.2 Hz 5° C. | G'/G" 0.2 Hz 5° C. | Complex viscosity, μ Pa, 25° C. 5 Hz | Phase Angle[3] δ, 5° C. 5 Hz |
|---|---|---|---|---|---|---|---|
| 1.2% Gelatin | 198 | 137 | 99 | 4.5 | 31 | 0.2 | 3.2 |
| 1.0% ex. 1 | 278 | 158 | 56 | 6.1 | 46 | 3.9 | 2.5 |
| 2% Gelatin[2] | 610 | 573 | 94 | 26 | 24 | 2.1 | 4.3 |

[1]Water dessert formulation pH = 4.3.
[2]The rheological data are based on one measurement, except for the gelling agent according to example 1 and gelatin (2%), where the data is the mean value of 3 measurements.
[3]The phase angle is given by the following formula: tan δ = G"/G'.

The following Table V shows rheological characteristics of certain Examples, including Examples 59–63. The examples were prepared as in Example 64, and the gelling agent was present at 1.2 wt % in each Example. That is, a solution having the following components (in parts per hundred by weight), was prepared for each example: fine sugar—15.00; tri-potassium citrate, monohydrate—0.30; calcium chloride, dihydrate—0.15; citric acid, anhydrous—0.20; gelling agent (carrageenan composition of the present invention or comparative carrageenan composition)—1.20; and demineralized water—83.15. The dry ingredients were weighed and mixed well and boiling water was added while stirring vigorously to form a solution. The solution was transferred hot to the cop of the Bohlin VOR theometer and tested as described above.

TABLE V

PHYSICAL CHARACTERISTICS OF INVENTIVE AND COMPARATIVE CARRAGEENAN COMPOSITIONS

| Example Number | Sample Treatment | Elastic Modulus G' - 1 Hz, 5° C. | Elastic Modulus G' - 1 Hz, 25° C. | Gel Strength Loss % ΔG' between 5° C. and 25° C. | Viscous Modulus G" - 0.2 Hz, 5° C. | Melting Point |
|---|---|---|---|---|---|---|
| 2 | 10% soda, 115° C., 3 h (concentrate), 2 h retention | 291 ± 10.5 | 136 ± 5.0 | 53 | 10.4 ± 0.4 | |
| 3 | 7% lime, 90° C., 45 min., neutralization HCl | 365 ± 1.4 | 161 ± 0.7 | 56 | 17.3 ± 0.2 | 60.8 |
| 4 | 9% soda, 115° C., 35 min. (concentrate), 18 h retention | 244 ± 9.5 | 126 ± 8.5 | 48 | 10.7 ± 7.6 | 54.5 |
| 8 | 13% potassium carbonate, 115° C., 3 h (concentrate), 2 h retention | 315 ± 5.7 | 177 ± 7.1 | 44 | 18.1 ± 1.9 | 52.0 |
| 12 | 7% lime, 100° C., 45 min., neutralization HCl | 401 ± 60.6 | 251 ± 5.7 | 37 | 19.7 ± 7.7 | 63.9 |
| 14 | 7% lime, 90° C., 120 min., neutralization HCl | 476 ± 2.8 | 263 ± 0.7 | 45 | 25.1 ± 1.7 | 65.5 |
| 17 | 10% soda, 115° C. 3 h (concentrate), 3–5 h retention. UF-conc. | 226 ± 15.6 | 162 ± 1.4 | 28 | 8.00 ± 1.4 | |
| 18 | 10% soda, 115° C. 3 h (concentrate), 3–5 h retention. UF-conc. | 232 ± 41.2 | 150 ± 0.7 | 36 | 7.68 ± 5.2 | 55.3 |
| 19 | 10% soda, 115° C. 3 h (concentrate), 3–5 h retention. UF-conc. | 221 ± 18.8 | 154 ± 10.4 | 31 | 8.55 ± 1.3 | |
| 20 | 5% soda, 115° C. 3 h (concentrate), 2 h retention | 287 ± 31 | 129 | 54 | | |
| 21 | 20% soda, 110° C., 35 min., grinding | 254 ± 7.1 | 177 ± 12.5 | 28 | 8.2 ± 2.3 | |
| 37 | 10.7% NH₄CO₃, 115° C., 3 h, 18 h retention | 66 ± 1.0 | 18.4 ± 0.2 | 72 | 0.92 ± 0.1 | |
| 41 | 5.4% NH₄CO₃, 115° C., 3 h, 2 h retention | 79.3 ± 4.1 | 23 ± 1.7 | 72 | 1.11 ± 0.2 | |
| 43 | Full calcium, 110° C. 35 min., no retention, neutralize, IE | 148 ± 8.7 | 120 ± 7.9 | 19 | 3.87 ± 1.0 | |
| 45 | Full calcium, 110° C. 35 min., no retention, neutralize, IE | 154 ± 2.5 | 127 ± 3.1 | 17 | 3.31 ± 0.5 | |
| 30 | Full calcium, 110° C. 35 min., no retention, neutralize, IE | 1382.8 | 108 ± 3.5 | 22 | 2.86 ± 0.6 | |
| 42 | Fully modified calcium Spinosum HF from plant | 109 ± 1.2 | 101 ± 1.0 | 8 | 0.98 ± 0.3 | |
| 52 | 7% lime, 100° C., 120 min., neutralization HCl | 255 ± 6.4 | 218 ± 0.7 | 14 | 13.2 ± 0.3 | 69.7 |
| 59 | 5% lime, 110° C., 35 min., 18 h | 126 ± 0.7 | 120 ± 0.7 | 5 | 4.66 ± 0.1 | |

TABLE V-continued

PHYSICAL CHARACTERISTICS OF INVENTIVE AND COMPARATIVE CARRAGEENAN COMPOSITIONS

| Example Number | Sample Treatment | Elastic Modulus G' - 1 Hz, 5° C. | Elastic Modulus G' - 1 Hz, 25° C. | Gel Strength Loss % ΔG' between 5° C. and 25° C. | Viscous Modulus G" - 0.2 Hz, 5° C. | Melting Point |
|---|---|---|---|---|---|---|
| 60 | 5% lime, 110° C., 35 min., 3 h retention, IE | 165 ± 10.6 | 146 ± 1.4 | 11 | 5.47 ± 0.7 | |
| 61 | 5% lime, 110° C., 35 min., 3 h retention, IE | 95 ± 2.1 | 60 ± 2.1 | 38 | 2.99 ± 0.1 | |
| 62 | 5% lime, 110° C., 35 min., 18 h retention, SUPER IE | 330 ± 1.4 | 200 ± 9.2 | 39 | 8.08 ± 0.4 | |
| 63 | 5% lime, 110° C., 35 min., 18 h retention, IE | 161 ± 14.0 | 118 ± 2.1 | 27 | 4.34 ± 1.9 | |

A second portion of the samples from Example 64 was poured into crystalizing dishes and allowed to cool and gel for measurement of textural properties outlined below. For the textural analysis, the gelling agent was present at 1.2 wt %. The gels were tested on a TA-XT2 Texture Analyzer, manufactured by Stable Micro Systems. This device was used for measurement of break strength, break distance, and negative area. Break Strength (BS) is the force (in grams) required to compress the gel to the point of break with a one inch diameter probe. Gel strength (GS) is the force (in grams) required to compress the gel to a predetermined depth of 2 mm, 8 mm, and 15 mm with a one inch diameter probe. Break distance (BD) is the distance (in mm) the probe travels to break a gel. In these experiments the probe speed is 1 mm/sec. Negative area (NA) is the area (g·sec) below the x-axis when a plot of force as a function of compression time is plotted as the probe withdrawn from the sample (see Tables VI–VIII).

TABLE VI

Measurements at 5° C.

| Sample | GS, 2 mm | GS, 15 mm | BS | BD | NA |
|---|---|---|---|---|---|
| Example 1 | 17.0 | 157.8 | 410.3 | 28.4 | −3460.5 |
| Compar. 1 | 7.2 | 66.8 | 147.8 | 24.5 | −1106.2 |
| Gelatin | 31.2 | 393.1 | 878.8 | 21.9 | −2885.8 |

TABLE VII

Measurements at 25° C.

| Sample | GS, 2 mm | GS, 15 mm | BS | BD | NA |
|---|---|---|---|---|---|
| Example 1 | 10.0 | 83.5 | 140.8 | 24.6 | −990.0 |
| Compar. 1 | 6.6 | 54.4 | 100.3 | 23.9 | −826.9 |
| Gelatin | 4.8 | 66.8 | 139.5 | 26.9 | −753.0 |

TABLE VIII

Change in % from 5° C. to 25° C.

| Sample | GS, 2 mm | GS, 15 mm | BS | BD | NA |
|---|---|---|---|---|---|
| Example 1 | 41 | 47 | 66 | 13 | 71 |
| Compar. 1 | 9 | 19 | 32 | 3 | 25 |
| Gelatin | 85 | 83 | 84 | −23 | 74 |

Dessert gels of the instant invention were also evaluated organoleptically by a trained sensory panel. The sensory profile analysis was conducted using an eleven member trained panel. The panel members were trained specifically for textural elements consistent with water desserts and gels, including 1) adhesiveness, 2) bounciness, 3) hardness, 4) cut through, 5) first bite, 6) brittleness, 7) cohesiveness, 8) flavor release, 9) gumminess, and 10) juiciness. Developed during the training were common language, gel attribute characterization and a 9 point (1 to 9) reference scale for the sensory attributes. During the evaluations, each sample was presented according to a standard balanced block design. Each panel member evaluated identical samples on two different occasions. Direct comparison of samples was impossible since all samples were presented one at a time. The final sensory scores were analyzed statistically and the overall grand average for each sample for each of the textural elements were generated.

Figure 3:
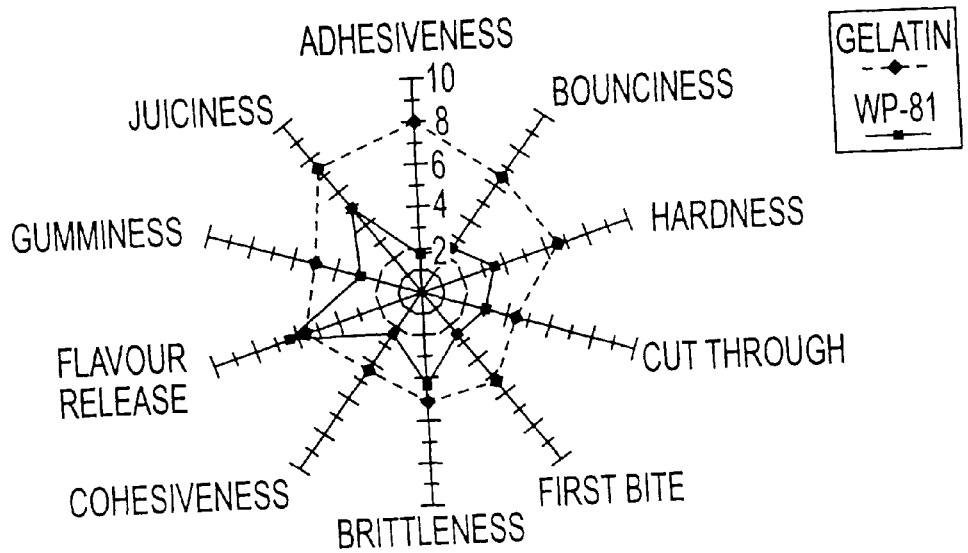
FIG. 3 shows a comparison between gelatin and commercially available carrageenan compositions (GENUGEL® Carrageenan type WP-81 (manufactured by Hercules Incorporated)) used in water desserts.
Figure 4:
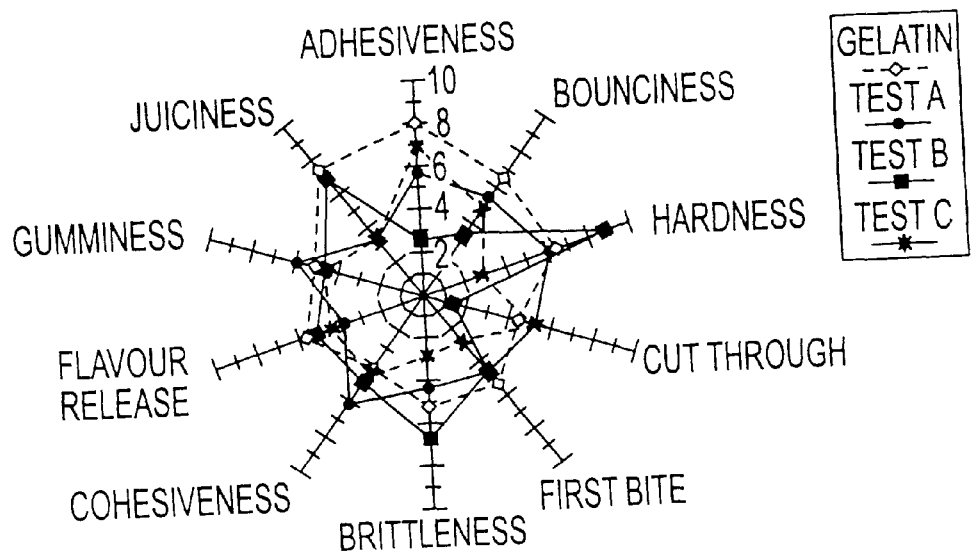
FIG. 4 shows a comparison between gelatin and carrageenan compositions of the instant invention used in water desserts.

FIGS. 3 and 4 illustrate the results of the trained sensory panel testing of water gels consistent with Example 1, Comparative Example 1 and gelatin, as well as other examples consistent with the carrageenan compositions described. FIG. 3 shows a comparison between gelatin and GENUGEL™ WP-81.

FIG. 4 shows a comparison of dessert gels produced in accordance with Example 64. For gelatin, the amount used is 2 parts by weight. For Test A, the gelling agent is 1.2 parts by weight, and comprises 93% carrageenan produced in accordance with Example 1, and 7% kappa carrageenan.

For Test B, the gelling agent is 0.462 parts by weight and comprises 53.7% carrageenan composition of Example 1, 27.6% kappa carrageenan, and 18.6% locust bean gum. In Test B, fine mesh (30 mesh) sugar is 15.738 parts by weight and demineralized water is 83.15 parts by weight.

For Test C, the gelling agent is 1.2 parts by weight, and the gelling agent comprises 100% of the carrageenan composition of Example 1.

From the results above, it is clear that the present invention, as embodied in Example 1, is superior in performance to other carrageenans, as embodied in Comparative Example 1.

The data for NA at 5° C. as well as at 25° C. also show that carrageenan compositions according to the present invention show a higher degree of adhesiveness and that the other carrageenan, particularly at 5° C., shows substantially lower adhesiveness. With respect to break strength, the carrageenan compositions according to the present invention produce break strengths considerably closer to gelatin than the other carrageenans, and when comparing the change in break strength from 5° C. to 25° C., it is seen that the carrageenan compositions according to the present invention show a substantially higher degree of temperature sensitivity than other carrageenans.

On the whole these results show that the present invention results in a carrageenan composition whose gel properties are considerably closer to those of gelatin than the gel properties of other carrageenans.

The preceding examples can be repeated with similar success by substituting the generically and specifically described constituents and/or operating conditions of this invention for those used in the preceding examples. From the foregoing descriptions, one skilled in the art can easily ascertain the essential characteristics of this invention, and without departing from the spirit and scope thereof, can make various changes and modifications of the invention to adapt it to various usages and conditions.

What is claimed is:

1. A composition comprising:
   from about 79 mol % to about 95 mol % iota carrageenan and from about 0.1 mol % to about 10 mol % nu carrageenan, when measured using $^{13}$C-NMR;
   exhibiting loss of elastic modulus, %ΔG' between 5° C. and 25° C., of greater than about 20%, in a 1.2 wt % aqueous gel; and
   exhibiting change in gel strength, 2 mm, from 5° C. to 25° C., of greater than about 20%, in a 1.2 wt % aqueous gel.

2. The composition of claim 1, comprising from about 82 mol % to about 92 mol % iota carrageenan, when measured using $^{13}$C-NMR.

3. The composition of claim 2, comprising from about 85 mol % to about 89 mol % iota carrageenan, when measured using $^{13}$C-NMR.

4. The composition of claim 1, comprising from about 3 mol % to about 8.5 mol % nu carrageenan, when measured using $^{13}$C-NMR.

5. The composition of claim 4, comprising from about 5 mol % to about 7 mol % nu carrageenan, when measured using $^{13}$C-NMR.

6. The composition of claim 1, wherein said composition exhibits a molecular weight of higher than about 600 kD, when measured with size exclusion chromatography, and as compared to poly(ethylene oxide) standards.

7. The composition of claim 6, wherein said composition exhibits a molecular weight of from about 600 kD to about 1,000 kD, when measured with size exclusion chromatography, and as compared to poly(ethylene oxide) standards.

8. The composition of claim 1, in combination with a gelling agent comprising at least one member selected from the group consisting of low-methoxyl pectin, locust bean gum, furcellaran, agar, gellan gum, kappa carrageenan, gelatin, xanthan gum, alginate, and combinations thereof.

9. The composition of claim 8, wherein the gelling agent comprises at least one member selected from the group consisting of kappa carrageenan and locust bean gum.

10. The composition of claim 1, exhibiting melting point of less than 60° C., in a 1.2 wt % aqueous gel.

11. The composition of claim 10, exhibiting melting point of from about 45° C. to less than 60° C., in a 1.2 wt % aqueous gel.

12. The composition of claim 10 exhibiting elastic modulus, G'—1 Hz at 5° C., of greater than about 200 Pa, in a 1.2 wt % aqueous gel.

13. The composition of claim 12, exhibiting elastic modulus, G'—1 Hz at 5° C., of from greater than about 200 Pa to about 400 Pa, in a 1.2 wt % aqueous gel.

14. The composition of claim 12, exhibiting elastic modulus, G'—1 Hz at 25° C., of less than about 200 Pa, in a 1.2 wt % aqueous gel.

15. The composition of claim 14, exhibiting elastic modulus, G'—1 Hz at 25° C., of from about 80 Pa to less than about 200 Pa, in a 1.2 wt % aqueous gel.

16. The composition of claim 14, exhibiting loss of elastic modulus, %ΔG' between 5° C. and 25° C., of from greater than about 20% to about 80%, in a 1.2 wt % aqueous gel.

17. The composition of claim 16, exhibiting viscous modulus, G"—0.2 Hz at 5° C., of greater than about 5 Pa, in a 1.2 wt % aqueous gel.

18. The composition of claim 17, exhibiting viscous modulus, G"—0.2 Hz at 5° C., of from greater than about 5 Pa to about 25 Pa, in a 1.2 wt % aqueous gel.

19. The composition of claim 1, exhibiting break strength, at 5° C., of from about 200 to about 600 g, in a 1.2 wt % aqueous gel.

20. The composition of claim 19, exhibiting break strength, at 25° C., of from about 110 to about 160 g, in a 1.2 wt % aqueous gel.

21. The composition of claim 20, exhibiting change in break strength, from 5° C. to 25° C., of from about 40 to about 80%, in a 1.2 wt % aqueous gel.

22. The composition of claim 21, exhibiting gel strength, 2 mm, at 5° C., of from about 10 to about 25 g, in a 1.2 wt % aqueous gel.

23. The composition of claim 22, exhibiting gel strength, 2 mm, at 25° C., of from about 7 to about 15 g, in a 1.2 wt % aqueous gel.

24. The composition of claim 23, exhibiting change in gel strength, 2 mm, from 5° C. to 25° C., of from greater than about 20 to about 60%, in a 1.2 wt % aqueous gel.

25. The composition of claim 24, exhibiting gel strength, 15 mm, at 5° C., of from about 100 to about 300 g, in a 1.2 wt % aqueous gel.

26. The composition of claim 25, exhibiting gel strength, 15 mm, at 25° C., of from about 60 to about 90 g, in a 1.2 wt % aqueous gel.

27. The composition of claim 26, exhibiting change in gel strength, 15 mm, from 5° C. to 25° C., of from greater than about 20 to about 60%, in a 1.2 wt % aqueous gel.

28. The composition of claim 27, exhibiting break distance, at 5° C., of from about 20 to about 30 mm, in a 1.2 wt % aqueous gel.

29. The composition of claim 28, exhibiting break distance, at 25° C., of from about 20 to about 26 mm, in a 1.2 wt % aqueous gel.

30. The composition of claim 29, exhibiting change in break distance, from 5° C. to 25° C., of from about 5 to about 20%, in a 1.2 wt % aqueous gel.

31. The composition of claim 30, exhibiting negative area, at 5° C., of from about −1500 to about −4000 g·sec, in a 1.2 wt % aqueous gel.

32. The composition of claim 31, exhibiting negative area, at 25° C., of from about −900 to about −1200 g·sec, in a 1.2 wt % aqueous gel.

33. The composition of claim 32, exhibiting change in negative area, from 5° C. to 25° C., of from about 50 to about 80%, in a 1.2 wt % aqueous gel.

34. A composition comprising:
   from about 79 mol % to about 95 mol % iota carrageenan and from about 0.1 mol % to about 10 mol % nu carrageenan, when measured using $^{13}$C-NMR, exhibiting elastic modulus, G'—1 Hz at 5° C., of greater than about 200 Pa, elastic modulus, G'—1 Hz at 25° C., of less than about 200 Pa, viscous modulus, G"—0.2 Hz at 5° C., of greater than about 5 Pa, and melting point of less than 60° C., in a 1.2 wt % aqueous gel.

35. The composition of claim 34, exhibiting a molecular weight of greater than about 600 kD when measured with size exclusion chromatography, as compared to poly (ethylene oxide) standards.

36. A method of producing a carrageenan composition comprising:

contacting carrageenan-containing material with a basic monovalent cationic solution under time, temperature, pH, and ionic conditions, to obtain carrageenan composition having from about 79 mol % to about 95 mol % iota carrageenan and from about 0.1 mol % to about 10 mol % nu carrageenan, when measured using $^{13}$C-NMR.

37. The method of claim 36 comprising:

contacting carrageenan-containing material with a basic monovalent cationic solution for a period of from about 10 minutes to about 200 minutes, at a temperature of from about 65° C. to about 135° C., wherein the basic monovalent cationic solution has a pH of from about 8 to about 11.5, and a concentration of carbonate or bicarbonate of from about 0.05 M to about 0.5 M, to obtain carrageenan composition having from about 79 mol % to about 95 mol % iota carrageenan and from about 0.1 mol % to about 10 mol % nu carrageenan, when measured using $^{13}$C-NMR.

38. The method of claim 36, wherein the basic monovalent cationic solution comprises at least one member selected from the group consisting of sodium carbonate, potassium carbonate, sodium bicarbonate, potassium bicarbonate, ammonium carbonate, and combinations thereof.

39. The method of claim 36, wherein the solution comprises carbonate or bicarbonate salt of monovalent cation in an amount which is from about 5% to about 20% of the dry weight of the starting material.

40. A method of producing a carrageenan composition comprising:

treating carrageenan-containing material with a basic monovalent cationic solution under time, temperature, pH, and ionic conditions, to obtain carrageenan composition exhibiting elastic modulus, G'—1 Hz at 5° C., of greater than about 200 Pa, elastic modulus, G'—1 Hz at 25° C., of less than about 200 Pa, viscous modulus, G"—0.2 Hz at 5° C., of greater than about 5 Pa, and melting point of less than 60° C., in a 1.2 wt % aqueous gel.

41. A carrageenan composition comprising iota carrageenan and nu carrageenan, exhibiting elastic modulus, G'—1 Hz at 5° C., of greater than about 200 Pa, elastic modulus, G'—1 Hz at 25° C., of less than about 200 Pa, viscous modulus, G"—0.2 Hz at 5° C., of greater than about 5 Pa, and melting point of less than 60° C., in a 1.2 wt % aqueous gel.

42. A method of producing a carrageenan composition comprising:

treating carrageenan-containing material with solution having a pH of from about 8 to about 11.5, at a temperature of from about 65° C. to about 90° C., for a period of from about 10 minutes to about 200 minutes, to produce from about 79 mol % to about 95 mol % iota carrageenan and from about 0.1 mol % to about 10 mol % nu carrageenan, when measured using $^{13}$C-NMR;

separating treated starting material from the solution;

adjusting the pH of the starting material;

washing treated starting material; and drying treated starting material.

43. A foodstuff comprising the composition of claim 1.

44. The foodstuff of claim 43, wherein the foodstuff comprises water desserts, milk desserts, or processed meat products.

45. The foodstuff of claim 43, comprising from about 0.4 to about 2.5 wt % carrageenan composition.

46. The foodstuff of claim 43, comprising from about 0.6 to about 1.3 wt % carrageenan composition.

47. An pharmaceutical preparation comprising the composition of claim 1.

48. The pharmaceutical preparation of claim 47, wherein the pharmaceutical preparation is an oral, topical, or veterinary pharmaceutical preparation.

49. A personal care product or household product comprising the composition of claim 1.

50. The product of claim 49, wherein the product comprises a skin care composition or toothpaste.

51. The personal care product of claim 49, wherein the product comprises air-freshener gel or cleaning gel.

52. A composition comprising iota carrageenan and nu carrageenan, wherein the molar ratio of iota carrageenan to nu carrageenan is greater than about 6:1;

exhibiting loss of elastic modulus, %ΔG' between 5° C. and 25° C., of greater than about 20%, in a 1.2 wt % aqueous gel; and exhibiting change in gel strength, 2 mm, from 5° C. to 25° C., of greater than about 20%, in a 1.2 wt % aqueous gel.

53. The composition of claim 52, wherein the molar ratio of iota carrageenan to nu carrageenan is from greater than about 6:1 to about 1000:1.

54. The composition of claim 53, wherein the molar ratio of iota carrageenan to nu carrageenan is from about 8:1 to about 100:1.

55. The composition of claim 54, wherein the molar ratio of iota carrageenan to nu carrageenan is from about 9:1 to about 25:1.

56. The composition of claim 55, wherein the molar ratio of iota carrageenan to nu carrageenan is from about 10:1 to about 20:1.

* * * * *